United States Patent
Gillis et al.

(10) Patent No.: US 9,439,801 B2
(45) Date of Patent: Sep. 13, 2016

(54) SYSTEMS AND METHODS FOR TREATMENT OF SLEEP APNEA

(75) Inventors: Edward M. Gillis, San Jose, CA (US); Csaba Truckai, Saratoga, CA (US); Paul J. Buscemi, Medina, MN (US)

(73) Assignee: ReVENT Medical, Inc., Newark, CA (US)

(*) Notice: Subject to any disclaimer, the term of this patent is extended or adjusted under 35 U.S.C. 154(b) by 402 days.

(21) Appl. No.: 13/539,081

(22) Filed: Jun. 29, 2012

(65) Prior Publication Data

US 2014/0000631 A1    Jan. 2, 2014

(51) Int. Cl.
*A61F 5/56* (2006.01)
*A61F 2/00* (2006.01)

(52) U.S. Cl.
CPC ............ *A61F 5/566* (2013.01); *A61F 2/00* (2013.01); *A61F 2210/0004* (2013.01); *A61F 2250/0018* (2013.01); *Y10T 29/49826* (2015.01)

(58) Field of Classification Search
USPC .......... 128/848, 859–862; 602/902; 433/6–7; 600/29–30, 216, 228
See application file for complete search history.

(56) References Cited

U.S. PATENT DOCUMENTS

| | | | |
|---|---|---|---|
| 4,424,208 A | 1/1984 | Wallace et al. | |
| 4,582,640 A | 4/1986 | Smestad et al. | |
| 4,978,323 A | 12/1990 | Freedman | |
| 5,041,138 A | 8/1991 | Vacanti et al. | |
| 5,145,935 A | 9/1992 | Hayashi | |
| 5,326,355 A | 7/1994 | Landi | |
| 5,372,600 A | 12/1994 | Beyar et al. | |
| 5,428,024 A | 6/1995 | Chu et al. | |
| 5,506,300 A | 4/1996 | Ward et al. | |
| 5,531,761 A * | 7/1996 | Yoon ........................ | 606/223 |
| 5,665,822 A | 9/1997 | Bitler et al. | |
| 5,697,779 A | 12/1997 | Sachdeva et al. | |
| 5,762,599 A | 6/1998 | Sohn | |
| 5,775,322 A | 7/1998 | Silverstein et al. | |
| 5,782,636 A | 7/1998 | Armstrong et al. | |
| 5,972,000 A | 10/1999 | Beyar et al. | |
| 5,972,111 A | 10/1999 | Anderson | |
| 5,979,456 A | 11/1999 | Magovern | |
| 5,988,171 A | 11/1999 | Sohn et al. | |
| 6,019,779 A | 2/2000 | Thorud et al. | |
| 6,161,541 A | 12/2000 | Woodson | |
| 6,165,486 A | 12/2000 | Marra et al. | |

(Continued)

FOREIGN PATENT DOCUMENTS

| EP | 1216013 B1 | 6/2006 |
|---|---|---|
| EP | 2561842 A1 | 2/2013 |

(Continued)

OTHER PUBLICATIONS

Jeon et al.; Shape memory and nonostructure in poly(norbornyl-POSS) copolymers; Polym Int; vol. 49(5); pp. 453-457; May 2000.

(Continued)

*Primary Examiner* — Ophelia A Hawthorne
(74) *Attorney, Agent, or Firm* — Shay Glenn LLP

(57) ABSTRACT

Methods of maintaining airway patency in an airway of a patient. A method includes the steps of wrapping a bioerodable material at least partway around an axis to create a wound bioerodable implant, and coupling two points on the bioerodable material to each other. The invention also provides systems for maintaining airway patency in an airway of a patient that may be used with the methods.

32 Claims, 35 Drawing Sheets

(56) References Cited

U.S. PATENT DOCUMENTS

| | | |
|---|---|---|
| 6,197,043 B1 | 3/2001 | Davidson |
| 6,231,605 B1 | 5/2001 | Ku |
| 6,250,307 B1 | 6/2001 | Conrad et al. |
| 6,388,043 B1 | 5/2002 | Langer et al. |
| 6,390,096 B1 | 5/2002 | Conrad et al. |
| 6,395,017 B1 | 5/2002 | Dwyer et al. |
| 6,401,717 B1 | 6/2002 | Conrad et al. |
| 6,415,796 B1 | 7/2002 | Conrad et al. |
| 6,431,174 B1 | 8/2002 | Knudson et al. |
| 6,439,238 B1 | 8/2002 | Brenzel et al. |
| 6,450,169 B1 | 9/2002 | Conrad et al. |
| 6,453,905 B1 | 9/2002 | Conrad et al. |
| 6,458,127 B1 | 10/2002 | Truckai et al. |
| 6,467,485 B1 | 10/2002 | Schmidt |
| 6,502,574 B2 | 1/2003 | Stevens et al. |
| 6,507,675 B1 | 1/2003 | Lee et al. |
| 6,513,530 B2 | 2/2003 | Knudson et al. |
| 6,513,531 B2 | 2/2003 | Knudson et al. |
| 6,516,806 B2 | 2/2003 | Knudson et al. |
| 6,523,541 B2 | 2/2003 | Knudson et al. |
| 6,523,542 B2 | 2/2003 | Knudson et al. |
| 6,530,896 B1 | 3/2003 | Elliott |
| 6,546,936 B2 | 4/2003 | Knudson et al. |
| 6,569,191 B1 | 5/2003 | Hogan |
| 6,578,763 B1 | 6/2003 | Brown |
| 6,601,584 B2 * | 8/2003 | Knudson et al. ............ 128/897 |
| 6,626,181 B2 | 9/2003 | Knudson et al. |
| 6,626,916 B1 | 9/2003 | Yeung et al. |
| 6,629,988 B2 | 10/2003 | Weadock |
| 6,634,362 B2 | 10/2003 | Conrad et al. |
| 6,636,767 B1 | 10/2003 | Knudson et al. |
| 6,703,040 B2 | 3/2004 | Katsarava et al. |
| 6,748,950 B2 | 6/2004 | Clark et al. |
| 6,748,951 B1 | 6/2004 | Schmidt |
| 6,772,944 B2 | 8/2004 | Brown |
| 6,899,105 B2 | 5/2005 | Krueger et al. |
| 7,017,582 B2 | 3/2006 | Metzger et al. |
| 7,063,089 B2 | 6/2006 | Knudson et al. |
| 7,090,672 B2 | 8/2006 | Underwood et al. |
| 7,107,992 B2 | 9/2006 | Brooks et al. |
| D536,792 S | 2/2007 | Krueger et al. |
| 7,192,443 B2 | 3/2007 | Solem et al. |
| 7,213,599 B2 | 5/2007 | Conrad et al. |
| 7,255,110 B2 | 8/2007 | Knudson et al. |
| 7,322,356 B2 | 1/2008 | Critzer et al. |
| 7,337,781 B2 | 3/2008 | Vassallo |
| 7,793,661 B2 | 9/2010 | Macken |
| 7,824,704 B2 | 11/2010 | Anderson et al. |
| 7,909,037 B2 | 3/2011 | Hegde et al. |
| 7,909,038 B2 | 3/2011 | Hegde et al. |
| 7,934,506 B2 | 5/2011 | Woodson et al. |
| 7,947,076 B2 | 5/2011 | Vassallo et al. |
| 7,992,567 B2 | 8/2011 | Hirotsuka et al. |
| 7,997,266 B2 | 8/2011 | Frazier et al. |
| 8,167,787 B2 | 5/2012 | Gillis |
| 8,186,355 B2 | 5/2012 | van der Burg et al. |
| 8,220,466 B2 | 7/2012 | Frazier et al. |
| 8,409,296 B2 | 4/2013 | Knize et al. |
| 8,528,564 B2 | 9/2013 | Paraschac et al. |
| 9,050,176 B2 | 6/2015 | Datta et al. |
| 9,161,855 B2 | 10/2015 | Rousseau et al. |
| 2001/0051815 A1 | 12/2001 | Esplin |
| 2002/0020417 A1 * | 2/2002 | Nikolchev et al. ............ 128/831 |
| 2002/0116050 A1 | 8/2002 | Kocur |
| 2002/0116070 A1 | 8/2002 | Amara et al. |
| 2003/0149445 A1 | 8/2003 | Knudson et al. |
| 2004/0045556 A1 | 3/2004 | Nelson et al. |
| 2004/0139975 A1 | 7/2004 | Nelson et al. |
| 2004/0204734 A1 | 10/2004 | Wagner et al. |
| 2005/0004417 A1 | 1/2005 | Nelson et al. |
| 2005/0065615 A1 | 3/2005 | Krueger et al. |
| 2005/0090861 A1 | 4/2005 | Porter |
| 2005/0092332 A1 | 5/2005 | Conrad et al. |
| 2005/0115572 A1 | 6/2005 | Brooks et al. |
| 2005/0121039 A1 | 6/2005 | Brooks et al. |
| 2005/0154412 A1 | 7/2005 | Krueger et al. |
| 2005/0171572 A1 * | 8/2005 | Martinez ..................... 606/200 |
| 2005/0199248 A1 | 9/2005 | Pflueger et al. |
| 2005/0267321 A1 | 12/2005 | Shadduck |
| 2005/0274384 A1 * | 12/2005 | Tran et al. .................... 128/831 |
| 2006/0150986 A1 | 7/2006 | Roue et al. |
| 2006/0201519 A1 | 9/2006 | Frazier et al. |
| 2006/0207606 A1 | 9/2006 | Roue et al. |
| 2006/0229669 A1 | 10/2006 | Mirizzi et al. |
| 2006/0235380 A1 | 10/2006 | Vassallo |
| 2006/0260623 A1 | 11/2006 | Brooks et al. |
| 2006/0289014 A1 | 12/2006 | Purdy et al. |
| 2006/0289015 A1 | 12/2006 | Boucher et al. |
| 2007/0010787 A1 | 1/2007 | Hackett et al. |
| 2007/0108077 A1 | 5/2007 | Lung et al. |
| 2007/0144534 A1 | 6/2007 | Mery et al. |
| 2007/0198040 A1 | 8/2007 | Buevich et al. |
| 2007/0261701 A1 | 11/2007 | Sanders |
| 2007/0288057 A1 | 12/2007 | Kuhnel |
| 2007/0295340 A1 | 12/2007 | Buscemi |
| 2008/0023012 A1 | 1/2008 | Dineen et al. |
| 2008/0027560 A1 | 1/2008 | Jackson et al. |
| 2008/0053461 A1 | 3/2008 | Hirotsuka et al. |
| 2008/0058584 A1 | 3/2008 | Hirotsuka et al. |
| 2008/0066764 A1 | 3/2008 | Paraschac et al. |
| 2008/0066765 A1 | 3/2008 | Paraschac et al. |
| 2008/0066766 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0078412 A1 | 4/2008 | Buscemi et al. |
| 2008/0082113 A1 | 4/2008 | Bishop et al. |
| 2008/0188947 A1 | 8/2008 | Sanders |
| 2009/0038623 A1 | 2/2009 | Farbarik et al. |
| 2009/0044814 A1 * | 2/2009 | Iancea et al. ................. 128/848 |
| 2009/0084388 A1 | 4/2009 | Bagley et al. |
| 2009/0126742 A1 | 5/2009 | Summer |
| 2009/0319046 A1 | 12/2009 | Krespi et al. |
| 2010/0037401 A1 | 2/2010 | Rousseau et al. |
| 2010/0132719 A1 * | 6/2010 | Jacobs et al. ................. 128/848 |
| 2010/0158854 A1 | 6/2010 | Puisais |
| 2010/0163056 A1 | 7/2010 | Tschopp et al. |
| 2011/0100377 A1 | 5/2011 | Weadock et al. |
| 2011/0144421 A1 | 6/2011 | Gillis |
| 2011/0166598 A1 | 7/2011 | Gonazles et al. |
| 2011/0174315 A1 | 7/2011 | Zhang et al. |
| 2011/0226262 A1 | 9/2011 | Gillis et al. |
| 2011/0226263 A1 | 9/2011 | Gillis et al. |
| 2011/0290258 A1 | 12/2011 | Pflueger et al. |
| 2011/0308529 A1 | 12/2011 | Gillis et al. |
| 2011/0308530 A1 | 12/2011 | Gillis et al. |
| 2012/0017919 A1 | 1/2012 | Gillis |
| 2012/0024298 A1 | 2/2012 | Gillis et al. |
| 2012/0132214 A1 | 5/2012 | Gillis |
| 2012/0138069 A1 | 6/2012 | Gillis et al. |
| 2012/0143134 A1 | 6/2012 | Hollis et al. |
| 2012/0180799 A1 | 7/2012 | Pflueger et al. |
| 2012/0197070 A1 | 8/2012 | Gillis |
| 2013/0056009 A1 | 3/2013 | Mohan et al. |
| 2013/0098374 A1 | 4/2013 | Gillis et al. |
| 2013/0109910 A1 | 5/2013 | Alexander et al. |
| 2013/0233324 A1 | 9/2013 | Witt et al. |
| 2013/0312767 A1 | 11/2013 | Gillis |
| 2013/0319427 A1 | 12/2013 | Sung et al. |
| 2014/0246027 A1 | 9/2014 | Gillis et al. |
| 2015/0032028 A1 | 1/2015 | Rampersaud et al. |
| 2015/0202074 A1 | 7/2015 | Gillis et al. |

FOREIGN PATENT DOCUMENTS

| | | |
|---|---|---|
| JP | 05-337126 A | 12/1993 |
| JP | 2604833 | 1/1997 |
| JP | 2001198147 | 7/2001 |
| JP | 2006507038 | 3/2006 |
| JP | 2007-97706 | 4/2007 |
| JP | 2007-512090 | 5/2007 |
| JP | 2007229485 | 9/2007 |
| JP | 2007525277 A | 9/2007 |
| WO | WO 97/18854 A1 | 5/1997 |

(56) References Cited

FOREIGN PATENT DOCUMENTS

| | | |
|---|---|---|
| WO | WO 99/00058 A1 | 1/1999 |
| WO | WO 00/66050 A1 | 11/2000 |
| WO | WO 01/89426 A1 | 11/2001 |
| WO | WO 02/13738 A1 | 2/2002 |
| WO | WO 02/076341 A2 | 10/2002 |
| WO | WO 02/076352 A1 | 10/2002 |
| WO | WO 02/076353 A1 | 10/2002 |
| WO | WO 02/076354 A1 | 10/2002 |
| WO | WO 03/041612 A2 | 5/2003 |
| WO | WO 03/055417 A1 | 7/2003 |
| WO | WO 03/065947 A1 | 8/2003 |
| WO | WO 2005/044158 A1 | 5/2005 |
| WO | WO 2006/012188 A1 | 2/2006 |
| WO | WO 2006/093533 A1 | 9/2006 |
| WO | WO 2006/101610 A2 | 9/2006 |
| WO | WO 2007/056583 A1 | 5/2007 |
| WO | WO 2007/070024 A2 | 6/2007 |
| WO | WO 2008/042058 A1 | 4/2008 |
| WO | WO 2008/097890 A2 | 8/2008 |
| WO | WO 2009/032625 A1 | 3/2009 |
| WO | WO 2010/028036 A1 | 3/2010 |
| WO | WO 2010/045546 A1 | 4/2010 |
| WO | WO 2010/051195 A1 | 5/2010 |
| WO | WO 2013/182893 A2 | 12/2013 |

OTHER PUBLICATIONS

Lui et al.; Thermomechanical characterization of a tailored series of shape memory polymers; J Applied Med Polymers; vol. 6/ No. 2; pp. 47-52; Sep. 2002.

Mather et al.; Strain recovery in POSS hybrid thermoplastics; Polymer Preprints; vol. 41, No. 1; pp. 528-529; 2000 (month unavailable).

Gillis; U.S. Appl. No. 14/282,943 entitled "Partially erodable systems for treatment of obstructive sleep apnea," filed May 20, 2014.

Gillis et al.; U.S. Appl. No. 14/289,475 entitled "Systems and methods for treatment of sleep apnea," filed May 28, 2014.

DeRowe et al.; A minimally invasive technique for tongue base stabilation in obstructive sleep apnea; Operative Techniques in Otolaryngology-Head and Neck Surgery; 11(1); pp. 41-46; Mar. 2000.

Miller et al.; Role of the tongue base supension suture with the Repose System bone screw in multileval surgical management of obstructive sleep apnea; Otolaryngol Head Neck Surg.; 126(4); pp. 392-398; Apr. 2002.

Walker et al.; Palatal implants for snoring and sleep apnea; Operative Techniques in otolaryngology; 17(4); pp. 238-241; Dec. 2006.

Woodson et al.; Pharyngeal suspension suture with Repose bone screw for obstructive sleep apnea; Otolaryngol Head Neck Surg.; 122(3); pp. 395-401; Mar. 2000.

Gillis et al.; U.S. Appl. No. 13/935,052 entitled "Systems and Methods for Treatment of Sleep Apnea," filed Jul. 3, 2013.

Gillis et al.; U.S. Appl. No. 13/939,107 entitled "Systems and Methods for Treatment of Sleep Apnea," filed Jul. 10, 2013.

Collins English Dictionary; "elastomer" (definition); Complete & Unabridged; 10th Edition; HarperCollins Publishers; May 11, 2015; retrieved from the Internet (http://dictionary.reference.com/browse/elastomeric>).

Gillis et al.; U.S. Appl. No. 14/877,862 entitled "Systems and methods for treatment of sleep apnea," filed Oct. 7, 2015.

\* cited by examiner

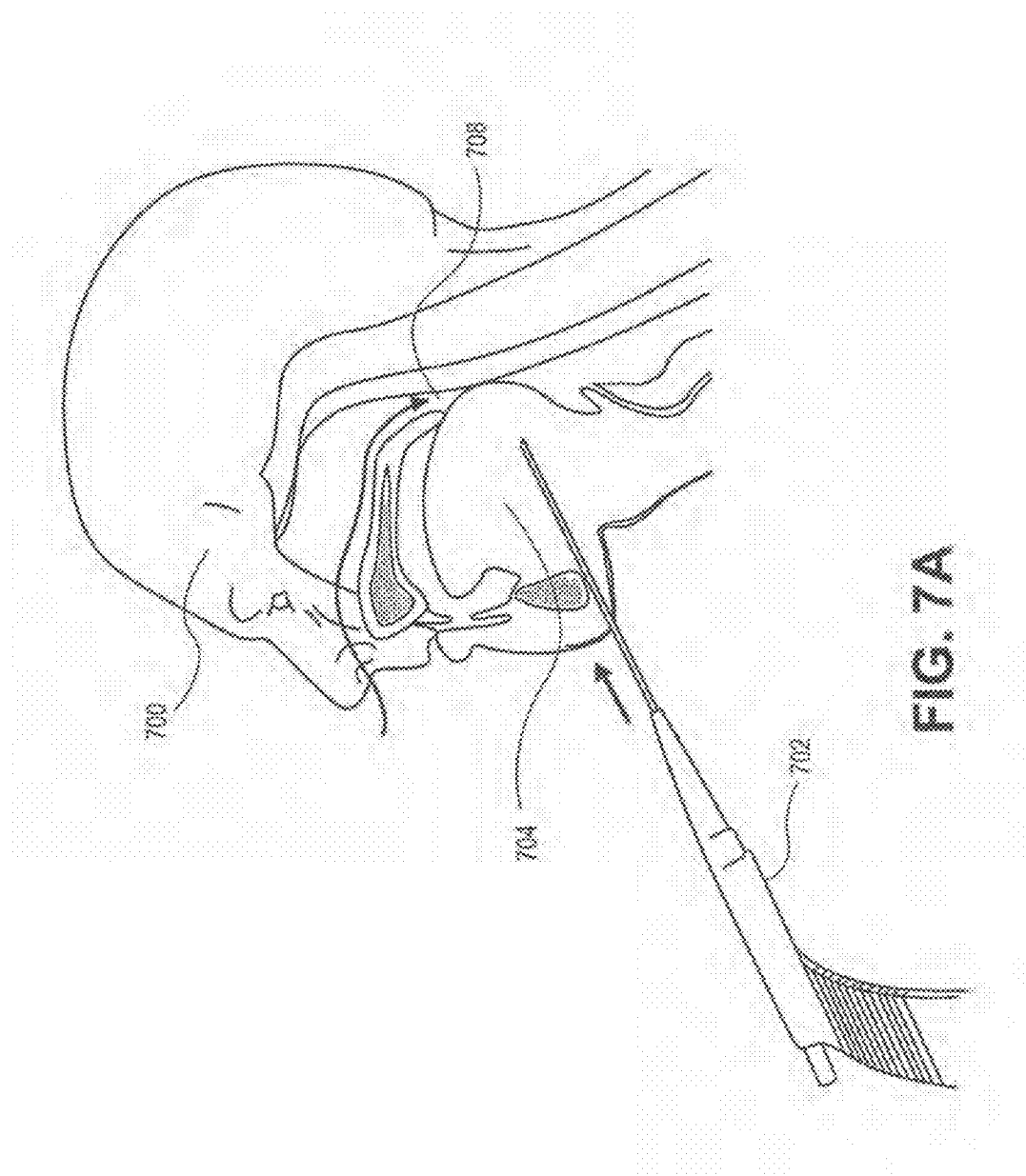

SYSTEMS AND METHODS FOR TREATMENT OF SLEEP APNEA

INCORPORATION BY REFERENCE

All publications and patent applications mentioned in this specification are herein incorporated by reference to the same extent as if each individual publication or patent application was specifically and individually indicated to be incorporated by reference.

FIELD

The disclosure relates to the field of methods and devices for the treatment of airway tissue disorders and more particularly to the treatment of obstructive sleep apnea, and opening the airway of subjects with symptoms of obstructive sleep apnea.

BACKGROUND

The invention relates to the field of methods and devices for the treatment of airway tissue disorders and more particularly to the treatment of obstructive sleep apnea and opening the airway of subjects with symptoms of obstructive sleep apnea.

Sleep apnea is defined as the cessation of breathing for ten seconds or longer during sleep. During normal sleep, the throat muscles relax and the airway narrows. During the sleep of a subject with obstructive sleep apnea (OSA), the upper airway narrows significantly more than normal, and during an apneic event, undergoes a complete collapse that stops airflow. In response to a lack of airflow, the subject is awakened at least to a degree sufficient to reinitiate breathing. Apneic events and the associated arousals can occur up to hundreds of times per night, and become highly disruptive of sleep. Obstructive sleep apnea is commonly but not exclusively associated with a heavy body type, a consequence of which is a narrowed oropharyngeal airway.

Cyclic oxygen desaturation and fragmented sleeping patterns lead to daytime sleepiness, the hallmark symptom of the disorder. Further consequences of sleep apnea may include chronic headaches and depression, as well as diminished facilities such as vigilance, concentration, memory, executive function, and physical dexterity. Ultimately, sleep apnea is highly correlated with increased mortality and life threatening comorbidities. Cardiology complications include hypertension, congestive heart failure, coronary artery disease, cardiac arrhythmias, and atrial fibrillation. OSA is a highly prevalent disease conditions in the United States. An estimated 18 million Americans suffer from OSA to degrees that range from mild to severe, many of whom are undiagnosed, at least in part because the afflicted subjects are often unaware of their own condition.

Treatment of OSA usually begins with suggested lifestyle changes, including weight loss and attention to sleeping habits (such as sleep position and pillow position), or the use of oral appliances that can be worn at night and help position the tongue away from the back of the airway. More aggressive physical interventions include the use of breathing assist systems (such as continuous positive airway pressure machines) that provide a positive pressure to the airway through a mask worn by the subject. In some cases, pharmaceutical interventions can be helpful, but they generally are directed toward countering daytime sleepiness and do not address the root cause. Some surgical interventions are available, such as nasal surgeries, tonsillectomy and/or adenoidectomy, reductions in the soft palate or the uvula or the tongue base, or advancing the tongue base by an attachment to the mandible and pulling the base forward. These surgical approaches can be quite invasive and thus have a last-resort aspect to them and simply do not reliably alleviate or cure the condition. There is a need for less invasive procedures that show promise for greater therapeutic reliability.

Related devices and methods are described in U.S. Pat. No. 8,167,787, U.S. 2011-0144421, U.S. 2011-0226262, and U.S. patent application Ser. No. 13/308,449 to Gillis et al. filed Nov. 30, 2011 the disclosures of which are incorporated herein by reference.

SUMMARY OF THE DISCLOSURE

The present invention provides methods and devices for treating obstructive sleep apnea, other sleep disorders, other airway problems or airway disorders, other jaw or throat problems or disorders such as snoring, other sleep-disordered breathing, other breathing difficulties, swallowing difficulties, or speech problems. Embodiments of the invention include methods for opening a collapsed or obstructed airway with devices that can be implanted into various tissues that form the airway. Embodiments of the devices include resiliently deformable materials and bioerodable materials. The deformable portion of the devices may be formed into a preferred shape and may then subsequently be deformed and stabilized in that deformed shape by incorporation or application of bioerodable materials to create a device in an implantable form. Once implanted into a tissue site, and thus exposed to an aqueous environment and to cellular and enzymatic action, the bioerodable portions of the device erode, thereby allowing the deformable portion of the device to return toward an at-rest form. Embodiments of the method, in their simplest form, thus include implanting a device, the bioerodable portion of the device bioeroding, the device changing shape as a consequence of the bioeroding, and the tissue remodeling in accordance with the force being exerted by the shape changing of the device.

One aspect of the invention provides a method of maintaining airway patency in an airway of a patient. The method includes the steps of implanting a device into airway-forming tissue without affixing the device to the tissue and permitting a bioerodable portion of the device to bioerode to apply a force to the airway-forming tissue to maintain airway patency. In some embodiments, the method also includes the step of expanding a portion of the device without affixing the device to the tissue, such as by, for example, permitting the portion of the device to self-expand. In various embodiments, the implanting step may include the step of inserting the device into the patient submandibularly, sublingually, and/or intra-orally.

In some embodiments, the permitting step includes the step of changing a shape of the device when the bioerodable portion bioerodes, such as by changing a length, curvature and/or width of the device. The method may also include the step of permitting newly formed tissue to infiltrate the device, possibly with the newly formed tissue at least partially infiltrating the device prior to applying a force to the airway-forming tissue.

In various embodiments, the implanting step includes the step of inserting the device into tongue tissue, soft palate tissue, pharyngeal wall tissue and/or epiglottis tissue. The method may also include the step of releasing a bioactive agent from the bioerodable portion as it bioerodes.

Another aspect of the invention provides a device for maintaining patency of an airway of a patient. In some embodiments, the device has a body having an at-rest shape and a deformed shape, the body being adapted to be implanted into airway-forming tissue of the patient, and proximal and distal anchors adapted to be implanted into the airway-forming tissue, without affixing the device to the tissue, and to be infiltrated by tissue to affix the anchors to the airway-forming tissue, with at least one bioerodable element maintaining the body in the deformed shape against a return force and the body being configured to return toward the at-rest shape upon erosion of the bioerodable element. In various embodiments, the body is sized and shaped to be inserted into tongue tissue, into soft palate tissue, and/or into pharyngeal tissue.

In various embodiments, the bioerodable element includes a coil and/or a C-shaped element. In some embodiments, at least one of the proximal and distal anchors is adapted to expand, possibly through self-expansion. One or more of the anchors may contain woven and/or non-woven material and may include through-holes to permit tissue in-growth. One or more of the anchors may also contain braided material.

In some embodiments, the device's deformed shape is longer, straighter and/or wider than its at-rest shape. The device may also have an elutable bioactive agent in some embodiments.

Another aspect of the invention provides an implant system for treating a sleep disorder including a bioerodable material and an elongate long term implant, the bioerodable material at least partially enveloping the elongate long term implant and resisting a compressive force of the long term implant, the bioerodable material including a first region having a first flexibility and a second region having a second flexibility that is less than the first flexibility. In some embodiments, the implant system includes a plurality of first regions having the first flexibility and a plurality of second regions having the second, lesser flexibility. In some embodiments, the second regions of lesser flexibility are configured to maintain the bioerodable material in an enveloping configuration relative to the elongate long term implant. In some embodiments, the regions of lesser flexibility are configured to substantially hold the bioerodable material in an initial shape for a period of time that is less than 16 weeks upon exposure to a body fluid (e.g. between 2 and 6 weeks or between 3 and 5 weeks).

In some embodiments, the bioerodable material includes a spring having a plurality of coils, and the first regions having the first flexibility include two coils of the spring.

In some embodiments, the second regions having the second, lesser flexibility include two points on the coils that are linked with each other.

In some embodiments, the elongate long term implant comprises a silicone material. In some embodiments, the bioerodable material includes a polymer based on lactic acid (e.g. poly(lactic acid) or poly(DL-lactic-co-glycolic acid)).

Another aspect of the invention provides an implant system for implanting in airway forming tissue including a bioerodable material and an elongate long term implant, the bioerodable material at least partially enveloping the elongate long term implant and linked between a first set of two points on the bioerodable material to form a first bridge. In some embodiments, the bioerodable material is configured to hold the elongate long term implant in an initial shape (e.g. a tensioned state).

In some embodiments the bioerodable material includes a spring having at least two coils and a plurality of points, and the first bridge connects two points on the spring. In some embodiments, the two points are on different coils at a first end of the spring. In some embodiments, the bioerodable material is linked between a second set of two points on a second set of coils of the spring to form a second bridge. In some of these embodiments the second set of coils is at a second end of the spring. In some of these embodiments, the first and second bridges are bioerodable.

In some embodiments, substantially each coil is linked to at least one other coil to form a plurality of bridges.

Yet another aspect of the invention provides a resilient elongate implant body having a first insertion shape and a second therapeutic shape, and a bioerodable material having two coils that at least partially envelop the resilient elongate implant body, and the coils are coupled together to form a coupled coil structure. In some embodiments, the bioerodable material is configured to hold the implant body in the initial insertion shape. In some of these embodiments, the bioerodable material includes additional coils continuous with the two coils to form a spring and the additional coils of the spring are wrapped around the implant body, and the two coils are at an end of the spring. In some of these embodiments, substantially each coil is coupled to at least one other coil.

Yet another aspect of the invention provides a method of manufacturing an implant system, the implant having an elongate implant body and a bioerodable support material configured to hold the elongate implant body in a first, elongate shape, the method including the steps of wrapping the bioerodable support material at least partway around the implant body, the bioerodable support material having two points on it, and coupling the two points with each other to create a coupled bioerodable support material.

Yet another aspect of the invention includes a method of manufacturing a bioerodable implant including the steps of wrapping a bioerodable material at least partway around an axis to create a wound bioerodable implant, the bioerodable material including two points, and coupling the two points to each other. In some embodiments, the wound bioerodable implant includes a helix and coupling includes heating the helix to fuse the two points.

In some embodiments, the axis includes an elongate long term implant, and the wrapping around an axis comprises wrapping the bioerodable material around the elongate long term implant to create an implant system. In some of these embodiments, the method includes applying an expansive force to the elongate long term implant with the bioerodable material to hold the long term implant in an initial shape.

In some embodiments, the coupling step includes attaching a bioerodable material to the two points to create a support strut. In some embodiments, the coupling step includes applying at least one of an adhesive, an other chemical, or an energy source to the bioerodable material. In some embodiments, the coupling step includes heating the bioerodable material to melt the two points together.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6B is an enlarged cross-section along the lines shown in FIG. 6A.

FIG. 6D is an enlarged cross-section along the lines shown in FIG. 6C.

FIG. 6F is an enlarged cross-section along the lines shown in FIG. 6E.

FIG. 6H is an enlarged cross-section along the lines shown in FIG. 6G.

FIG. 6J is a cross-section along the lines shown in FIG. 6I.

FIGS. 7A-C show implantation and use of an airway-maintaining device delivered submandibularly.

FIGS. 19 C-D show two views of a device, such as that shown in FIGS. 19 A-B, after foreshortening.

DETAILED DESCRIPTION

Figure 1:
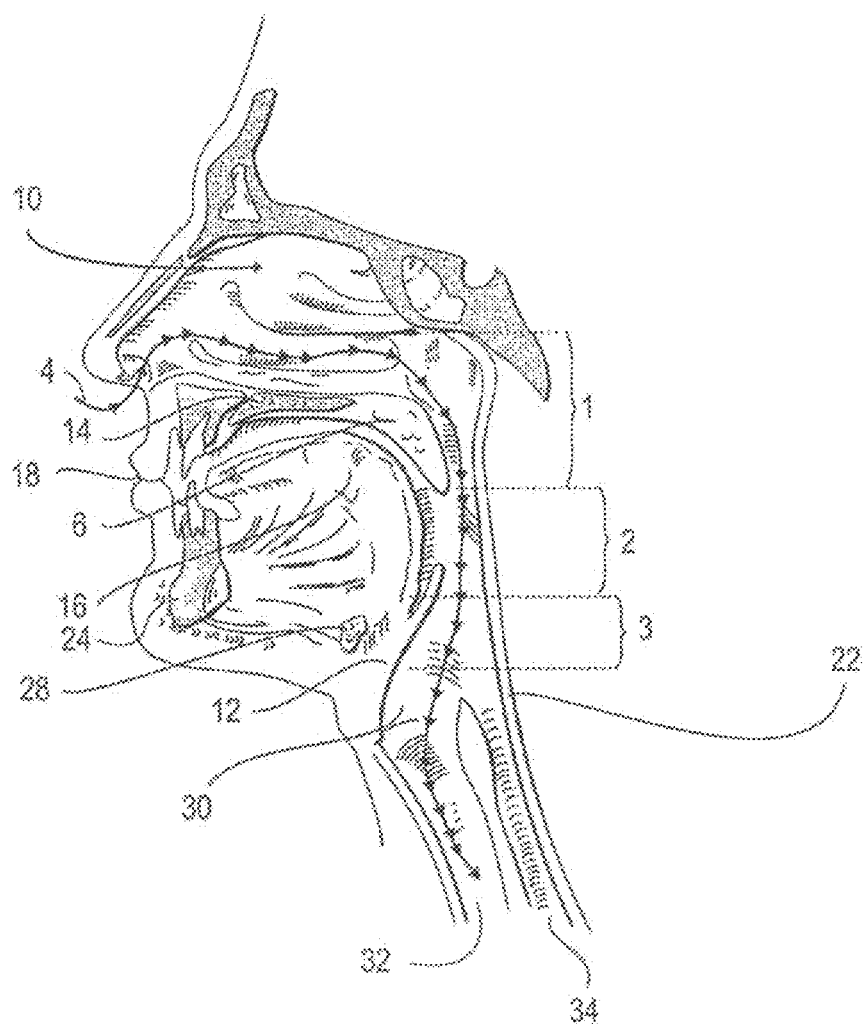
FIG. 1 shows an overview of the healthy human airway anatomy, with particular attention to the nasopharyngeal, oropharangeal, and hypopharyngeal regions.
Figure 2:
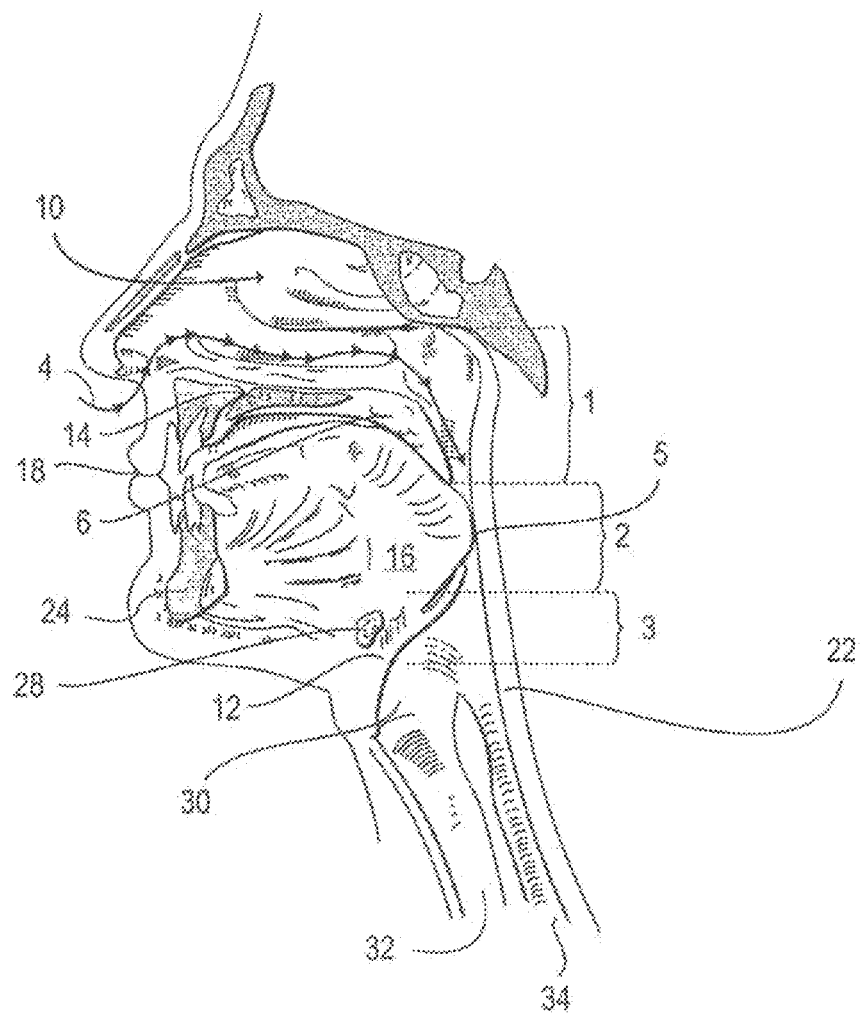
FIG. 2 provides a view of a compromised airway, with an occlusion in the oropharyngeal region due to posterior slippage of the base of the tongue and a thickened posterior pharyngeal wall.
Figure 3:
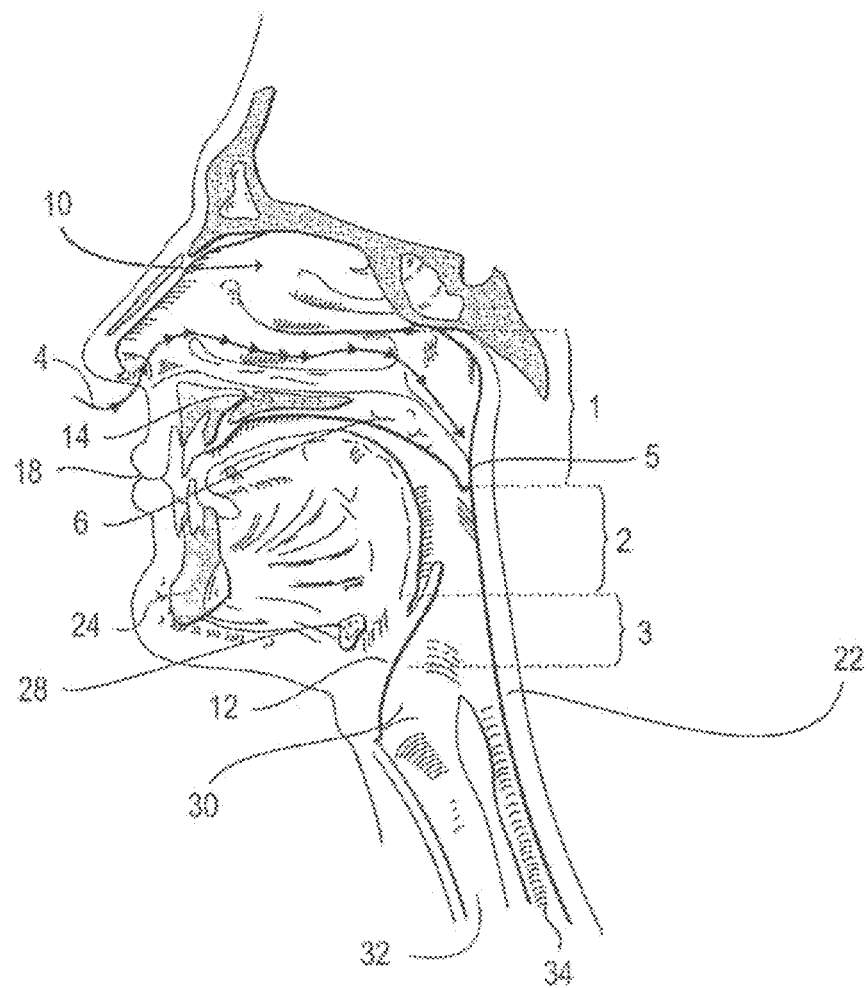
FIG. 3 provides a view of a compromised airway, with an occlusion in the nasopharyngeal region due to posterior slippage of the soft palate.
Figure 4:
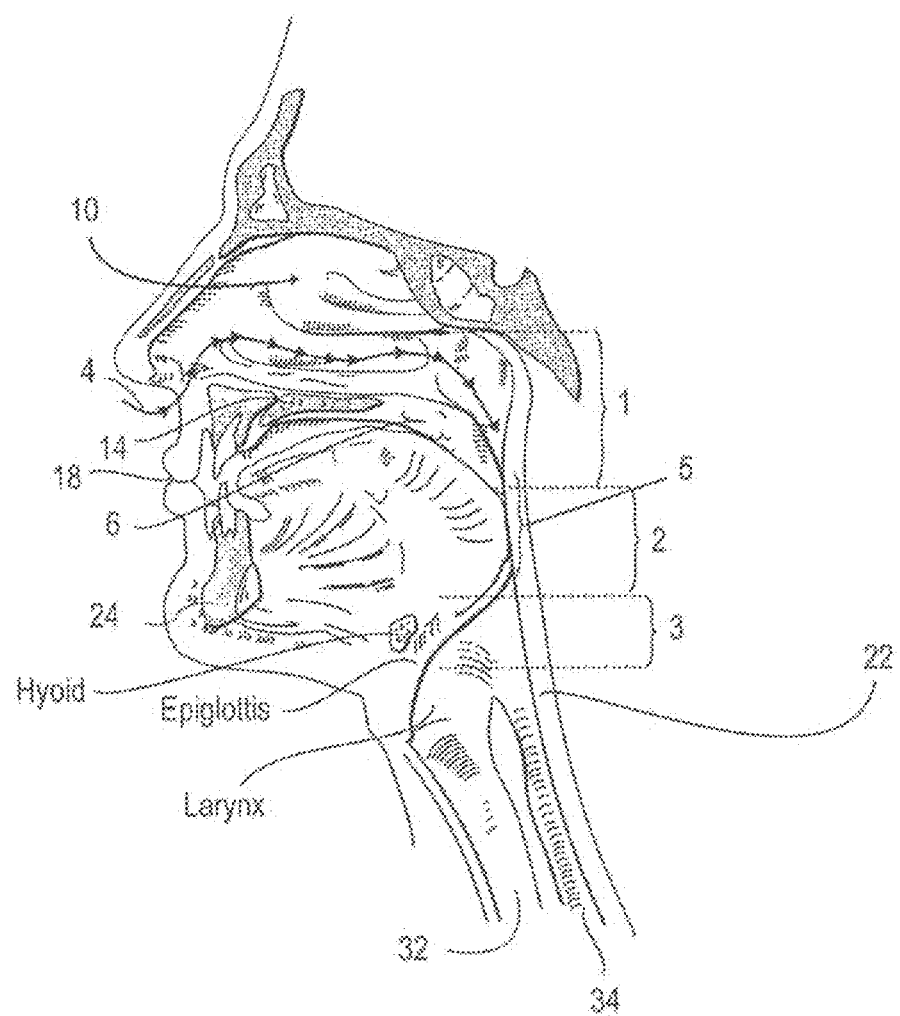
FIG. 4 provides a view of a compromised airway, with an occlusion in the oropharyngeal region due to posterior slippage of the base of the tongue and the soft palate, a thickened posterior pharyngeal wall, and posterior flopping of the epiglottis.

FIG. 1 is a sagittal view of the structures that form the pharyngeal airway 4. One or more of these structures can become compromised under various conditions to the extent that it (they) obstructs or occludes passage of air through airway 4 and thus contributes to obstructive sleep apnea. These or other causes may contribute to other sleep disorders, other airway problems or airway disorders or jaw or throat problems or disorders and may include snoring, other sleep-disordered breathing, other breathing difficulties (during sleep or wakefulness, difficulty swallowing, or speech problems. The pharynx is divided, from superior to inferior, into the nasopharynx 1, the oropharynx 2 and the hypopharynx 3. Variations of FIG. 1 are provided in FIGS. 2, 3, and 4, which depict airway obstruction sites 5 at various levels in the pharyngeal airway. FIG. 2, for example, shows an occlusion 5 at the level of the oropharynx 2, where the base of the tongue 16 and a thickened posterior pharyngeal wall 22 have collapsed against each other. FIG. 3 shows an occlusion 5 at the level of the nasopharynx 1, where an elongated and/or floppy soft palate 6 has collapsed against a thickened posterior pharyngeal wall 22. FIG. 4 shows an occlusion 5 at the level of the oropharynx and nasopharynx 1 and 2, where both an elongated soft palate 6, base of tongue 16 and a floppy epiglottis 12 have collapsed against the pharyngeal wall 22.

With reference to FIGS. 1-4, the nasopharynx 1 is the portion of the pharynx at the level or above the soft palate 6. In the nasopharynx, a deviated nasal septum or enlarged nasal turbinates 10 may occasionally contribute to upper airway resistance or blockage. Rarely, a nasal mass, such as a polyp, cyst or tumor may be a source of obstruction. The oropharynx 2 includes structures from the soft palate 6 to the upper border of the epiglottis 12 and includes the inferior surface of the hard palate 14, tongue 16, tonsils 18, palatoglossal arch 20, the posterior pharyngeal wall 22 and the mandible 24. The mandible typically has a bone thickness of about 5 mm to about 10 mm anteriorly with similar thicknesses laterally. An obstruction in the oropharynx 2 may result when the tongue 16 is displaced posteriorly during sleep as a consequence of reduced muscle activity during deep or non-REM sleep. The displaced tongue 16 may push the soft palate 6 posteriorly and may seal off the nasopharynx 1 from the oropharynx 2. The tongue 16 may also contact the posterior pharyngeal wall 22, which causes further airway obstruction.

The hypopharynx 3 includes the region from the upper border of the epiglottis 12 to the inferior border of the cricoid cartilage 14. The hypopharynx 3 further includes the hyoid bone 28, a U-shaped, free-floating bone that does not articulate with any other bone. The hyoid bone 28 is attached to surrounding structures by various muscles and connective tissues. The hyoid bone 28 lies inferior to the tongue 16 and superior to the thyroid cartilage 30. A thyrohyoid membrane 17 and a thyrohyoid muscle 18 attaches to the inferior border of the hyoid 28 and the superior border of the thyroid cartilage 30. The epiglottis 12 is infero-posterior to the hyoid bone 28 and attaches to the hyoid bone by a median hyoepiglottic ligament. The hyoid bone attaches anteriorly to the infero-posterior aspect of the mandible 24 by the geniohyoid muscle.

The invention provides a method of and devices for maintaining airway patency in an airway of a patient by implanting one or more devices into airway-forming tissue and permitting a bioerodable portion of the device to bioerode, thereby applying a force to the airway-forming tissue to maintain airway patency due to, e.g., a curvature, length or width change in the device. The method may be used and/or a device may be implanted to treat a sleep disorder, snoring or any other disorder, condition or disease or to otherwise alter a shape or response of a tissue. In some embodiments, the device or devices are implanted without initially affixing the device to the tissue. Over time, tissue growth or ingrowth into the devices may provide some fixation of the devices to the airway-forming tissue prior to the bioerosion and the device shape change. Various embodiments of shape-changing implants may be used to practice the invention, and the devices may be implanted into various parts of the patient's airway-forming tissue and for various reasons, as needed.

Figure 5A:
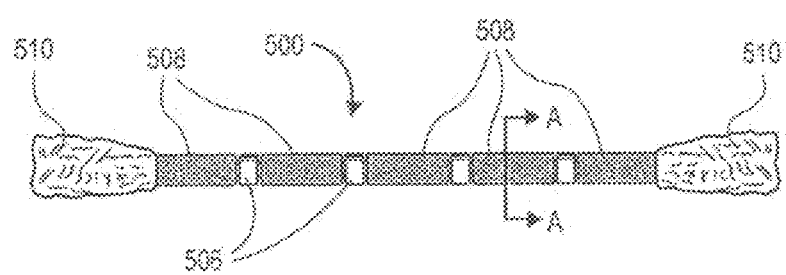
FIGS. 5A-C show an airway-maintaining device according to one embodiment of the invention.
Figure 5B:
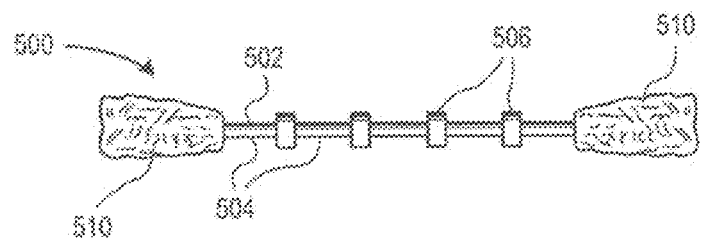
Figure 5C:
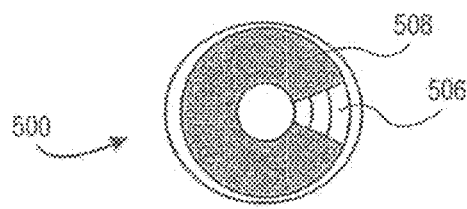

FIGS. 5A-C show one embodiment of a device 500 that may be implanted in airway-forming tissue to maintain patency of the patient's airway. Device 500 has a body 502 with a plurality of narrow sections 504 separated by wide sections 506. As shown, the narrow and wide sections are cylindrical, although other shapes may be used. The body 502 may be made of a resiliently deformable material, such as silicone rubber, polyurethanes or other resiliently deformable polymer or a coil of stainless steel, spring steel, or superelastic nickel-titanium alloy or other resiliently deformable metal, or a composite of the resiliently deformable polymer and metal.

FIG. 5B shows body 502 in its at-rest shape. In FIG. 5A, body 502 has been stretched to a deformed shape. Spacers 508 formed from a bioerodable or bioabsorbable material (such as, e.g., polycaprolactone, polylactic acid, polyglycolic acid, polylactide coglycolide, polyglactin, poly-L-lactide, polyhydroxalkanoates, starch, cellulose, chitosan, or structural protein) have been inserted between wide sections 506 to maintain the device in its deformed shape. In this embodiment, the spacers 508 are injection molded and have a C shape, although other manufacturing techniques and other shapes may be used as desired.

Anchors 510 are formed at both ends of body 502. In this embodiment, anchors 510 are formed from a non-woven fabric (such as polypropylene, polyethylene, or polyester) to promote tissue ingrowth. Other anchors may be used, as desired.

Device 500 may be implanted in a patient's airway-forming tissue in the deformed shape shown in FIG. 5A. In some embodiments, the device 500 is not affixed to the airway-forming tissue when implanted. Over time, tissue may grow into the fabric of anchors 510 to at least partially affix the device to the airway-forming tissue. Also over time, the bioerodable spacers 508 will bioerode, thereby permitting device 500 to move back toward the at-rest form shown in FIG. 5A. As it attempts to return to its at-rest shape, device 500 exerts a force on the airway-forming tissue into which it is implanted to maintain the patient's airway in a patent condition.

FIGS. 6A-J show various other embodiments of the invention in their deformed states. As in the embodiment of FIG. 5, these devices for maintaining patency of an airway may be implanted into airway-forming tissue of the patient in the illustrated deformed state. Over time, tissue may grow into the device anchors and possibly other parts of the device to at least partially affix the device to the airway-forming tissue. Also over time, the bioerodable spacer portions of the device may bioerode, thereby permitting the device to attempt to move toward a shorter at-rest shape, thereby exerting a force on the airway-forming tissue into which it is implanted to maintain the patient's airway in a patent condition. The deformable bodies of these devices may be formed, e.g., of silicone rubber.

Figures 6A, 6B, 6C, 6D, 6E, 6F, 6G, 6H, 6I, 6J:
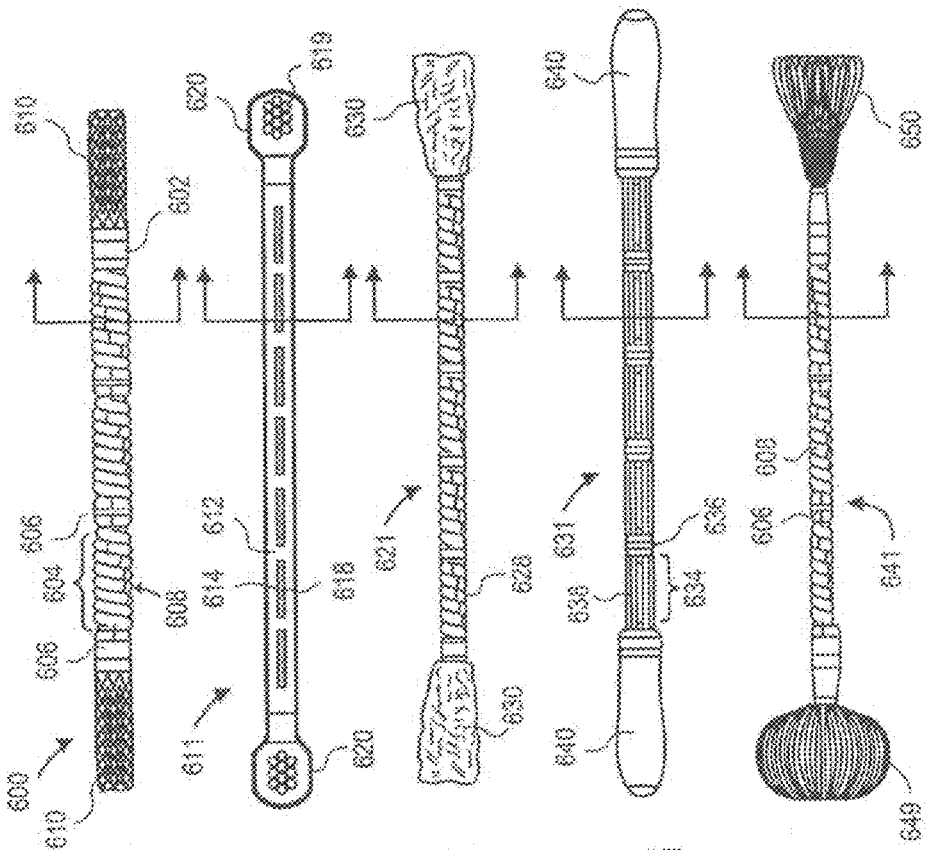
FIGS. 6A-B show an airway-maintaining device according to another embodiment of the invention.
FIGS. 6C-D show an airway-maintaining device according to yet another embodiment of the invention.
FIGS. 6E-F show an airway-maintaining device according to still another embodiment of the invention.
FIGS. 6G-H show an airway-maintaining device according to another embodiment of the invention.
FIGS. 6I-J show an airway-maintaining device according to yet another embodiment of the invention.

In FIGS. 6A-B, device 600 has a stiff bioerodable fiber 608 helically wound within narrow sections 604 of a resiliently deformable body 602 between wide sections 606 to maintain body 602 in its stretched deformed state. Fiber 608 may be made, e.g., of polyglactin 910, which is a copolymer of 90% glycolide and 10% L-lactide. When fiber 608 bioerodes, body 602 will attempt to shorten to its at-rest shape. Anchors 610 are disposed at both ends of body 602. Anchors 610 may be formed from woven polyester, polyethylene or polypropylene to provide for tissue ingrowth.

FIGS. 6C-D show a device 611 having a resiliently deformable body 612 in which a plurality elongated openings 614 are formed. In the depicted deformed state, bioerodable, rod shaped, spacers 618 (formed from, e.g., polylactidecoglycolide (PLG)) are disposed in the openings 614 to maintain the body's elongated deformed shape. Paddle-shaped anchor regions 620 having a plurality of holes or depressions 619 are disposed at both ends of body 612. Holes or depressions 619 permit tissue in-growth. Anchor regions 620 may be integral with the central portion of body 612 or may be formed from a different material, such as reinforced polyester. Anchor regions also may be integral with the central portion of body 612 and contain a composite reinforcing element such as a polyester fabric.

FIGS. 6E-F show a device 621 similar to that shown in FIGS. 5A-C in which the bioerodable portion 628 is formed of a helically wound bioerodable fiber, such as that discussed above with respect to FIGS. 6A-B and contains anchoring regions 630 of non woven fabric (e.g. polyester, polyethylene, or polypropylene).

FIGS. 6G-H show a device 631 having a resiliently deformable body 632 similar to body 602 of FIG. 6A. As shown, body 632 is in a stretched deformed shape. Bioerodable spacers 638 (similar to those of the embodiment shown in FIG. 5A) are disposed in narrow portions 634 between wide portions 636 to maintain body in this stretched shape. Anchors 640 on both ends are formed from an open or closed cell foam material to promote tissue in-growth.

FIGS. 6I-J show a device 641 substantially the same as the device shown in FIGS. 6E-F with the exception of the anchors 649 and 650. In this embodiment, anchors 649 and 650 are self-expanding baskets that can be compressed to the form shown as anchor 650 during implantation and will self-expand toward the at-rest shape shown as anchor 649 after deployment. The open areas of the anchors provide material loops and spaces for tissue ingrowth and attachment.

Other embodiments of the airway maintaining device may use various aspects of the illustrated embodiments as needed. For example, the anchors at end of the device body may differ from each other.

Figure 7B:
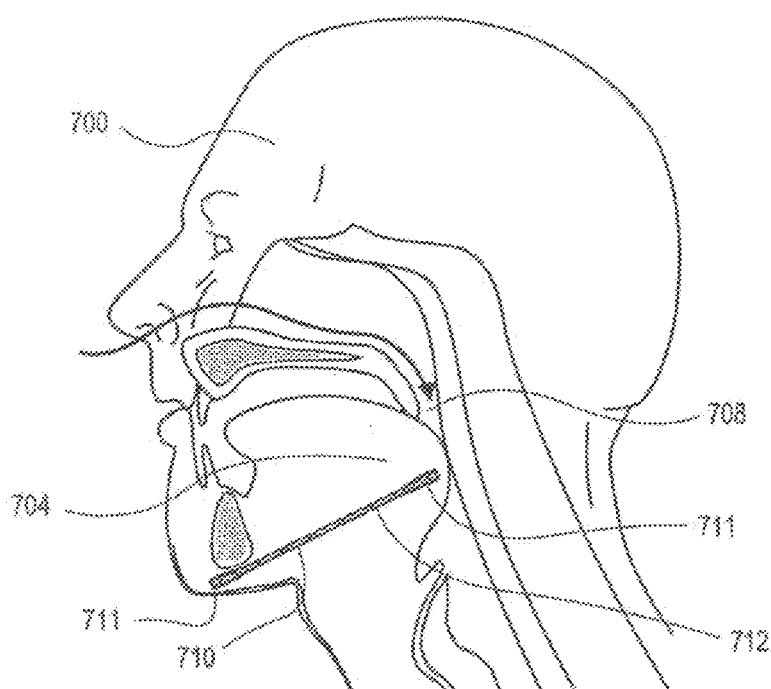
Figure 7C:
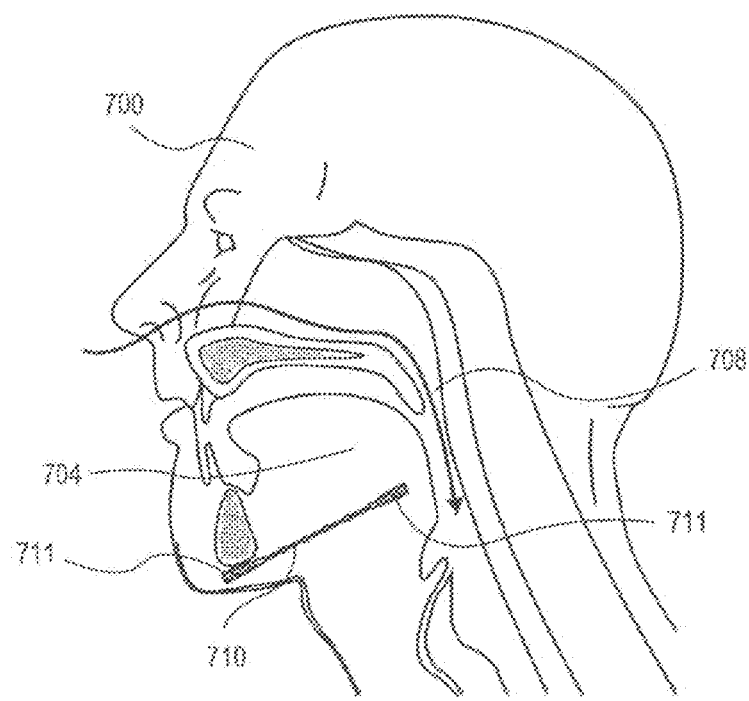

FIGS. 7-9 illustrate therapy provided by embodiments of this invention. In FIGS. 7A-C, a delivery tool 702 has been inserted submandibularly into the patient 700 to deliver an airway maintaining device 710 into a region of the patient's tongue 704 forming part of the patient's airway 708, which is shown as being blocked in FIG. 7A. Device 710 may be, e.g., any of the devices discussed above with respect to FIGS. 5 and 6. As shown in FIG. 7B, the device 710 is delivered in an elongated deformed state. In some embodiments, device 710 when first delivered is not affixed to the tongue tissue. Over time, however, tissue may grow into the anchors 711 of device 710 and/or other parts of the device. Also over time, bioerodable portions 712 of device 710 will bioerode, thereby permitting device 710 to move toward a shorter at-rest shape, thereby applying a force to the patient's tissue to maintain the patency of the airway, as shown in FIG. 7C.

Figure 8A:
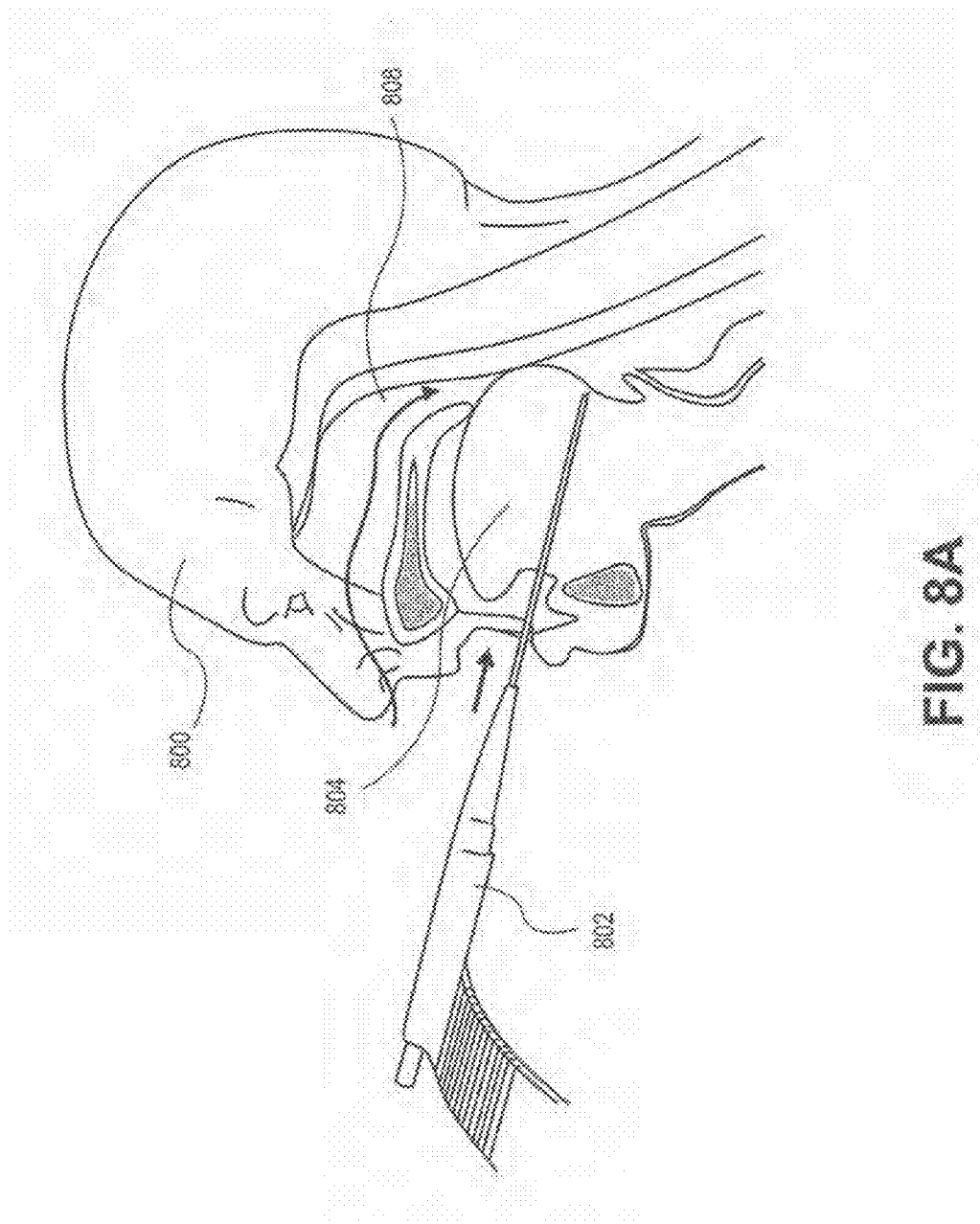
FIGS. 8A-C show implantation and use of an airway-maintaining device delivered intraorally and sublingually.
Figure 8B:
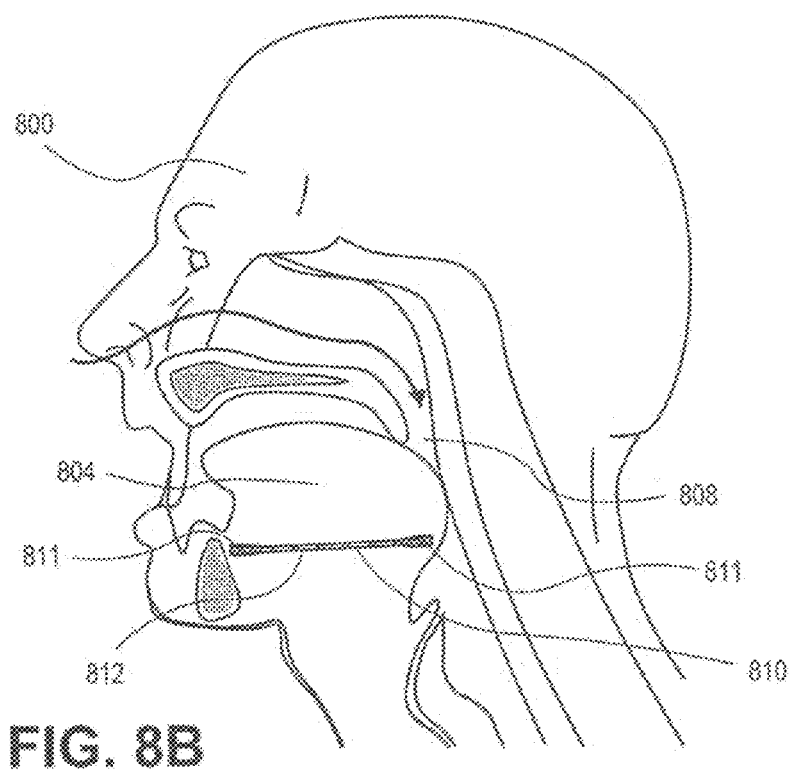
Figure 8C:
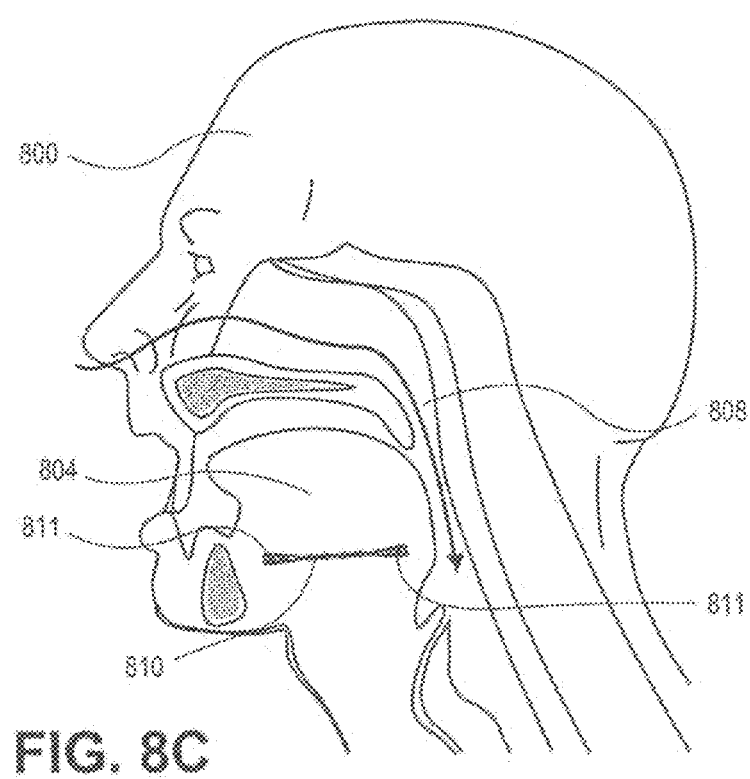

In FIGS. 8A-C, a delivery tool 802 has been inserted intraorally and sublingually into the patient 800 to deliver an airway maintaining device 810 into a region of the patient's tongue 804 forming part of the patient's airway 808, which is shown as being blocked in FIG. 8A. Device 810 may be, e.g., any of the devices discussed above with respect to FIGS. 5 and 6. As shown in FIG. 8B, the device 810 is delivered in an elongated deformed state. In some embodiments, device 810 when first delivered is not affixed to the tongue tissue. Over time, however, tissue may grow into the anchors 811 of device 810 and/or other parts of the device. Also over time, bioerodable portions 812 of device 810 will bioerode, thereby permitting device 810 to move toward a shorter at-rest shape, thereby applying a force to the patient's tissue to maintain the patency of the airway, as shown in FIG. 8C.

Figure 9A:
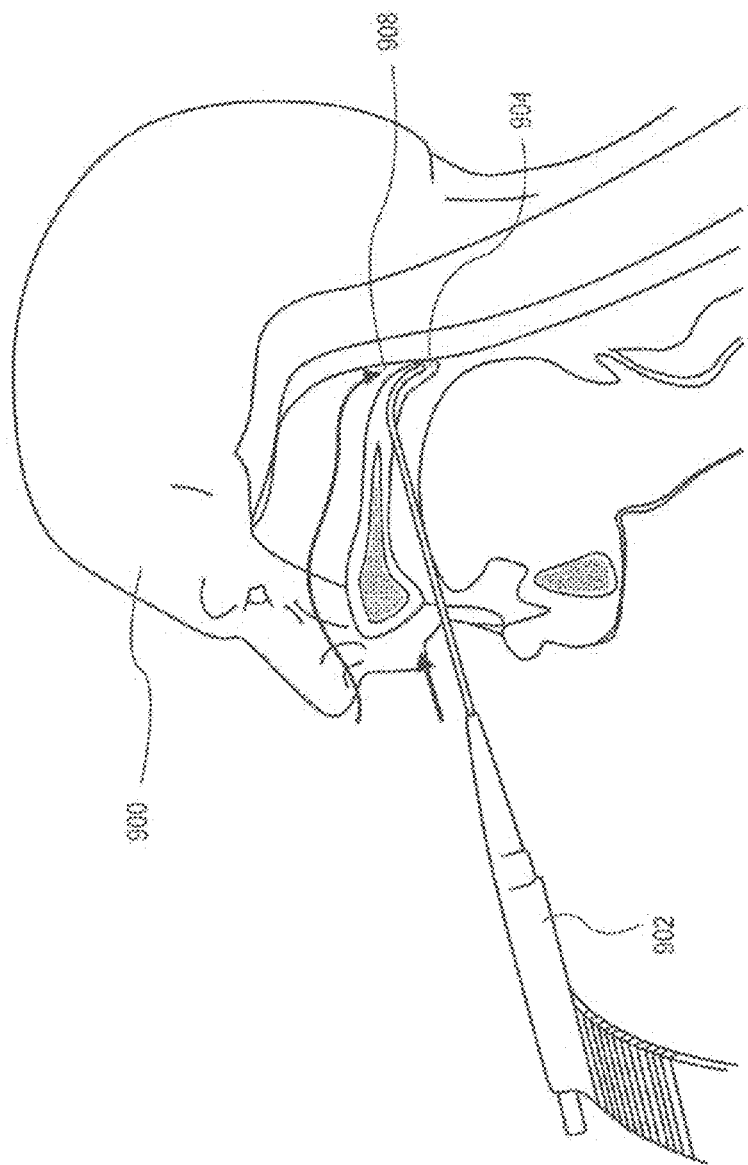
FIGS. 9A-C show implantation and use of an airway-maintaining device delivered intraorally to the soft palate.
Figure 9B:
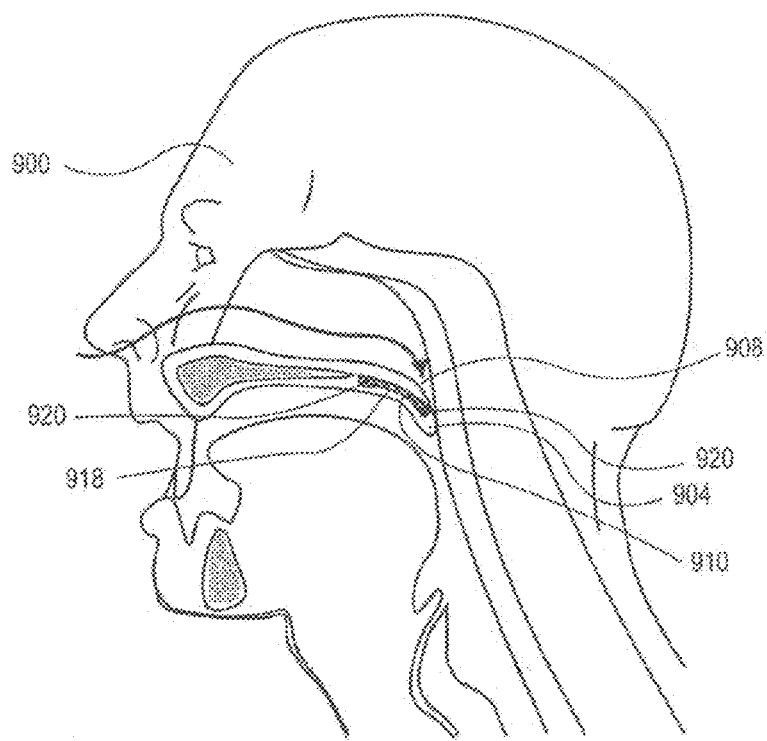
Figure 9C:
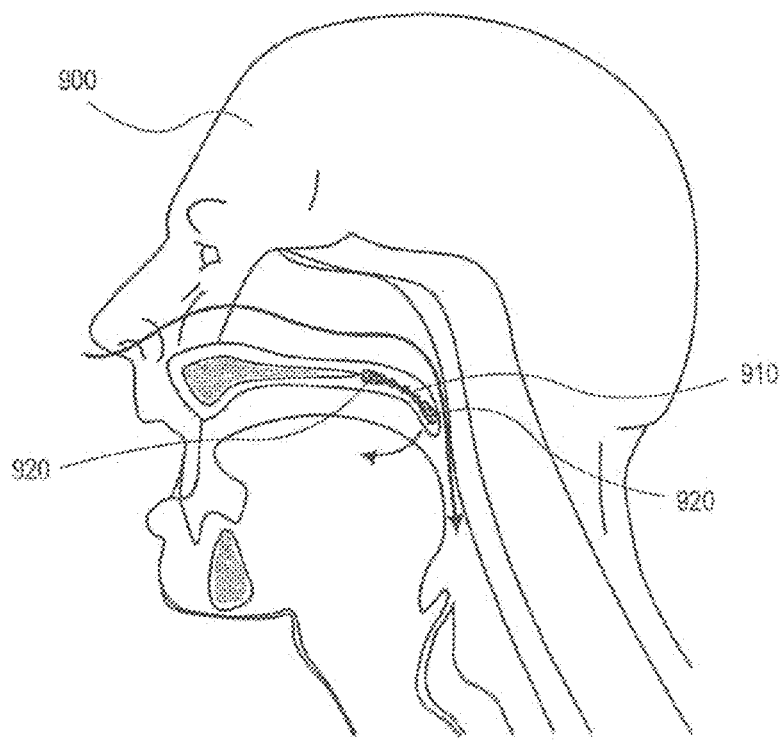

In FIGS. 9A-C, a delivery tool 902 has been inserted intraorally into the patient 900 to deliver an airway maintaining device 910 into a region of the patient's soft palate 904 forming part of the patient's airway 908, which is shown as being blocked in FIG. 9A. Device 910 is described in further detail below with respect to FIGS. 10 and 11. As shown in FIGS. 9B and 11A, the device 910 is delivered in an elongated and straightened deformed state. In some embodiments, device 910 when first delivered is not affixed to the soft palate tissue. Over time, however, tissue may grow into the anchors 920 of device 910 and/or other parts of the device. Also over time, bioerodable portions 918 of device 910 will bioerode, thereby permitting device 910 to move toward a shorter and more curved at-rest shape, thereby applying a force to the patient's soft palate tissue to maintain the patency of the airway, as shown in FIGS. 9C and 11B.

Figure 10A:
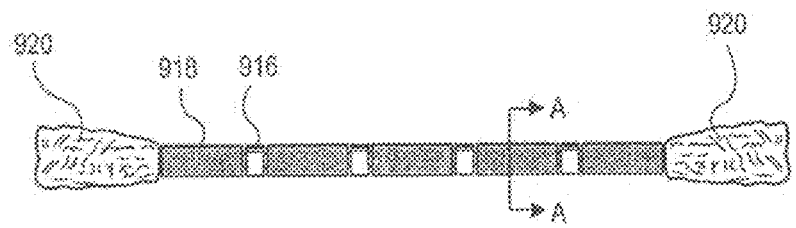
FIGS. 10A-C show details of the device shown in FIG. 9.
Figure 10B:
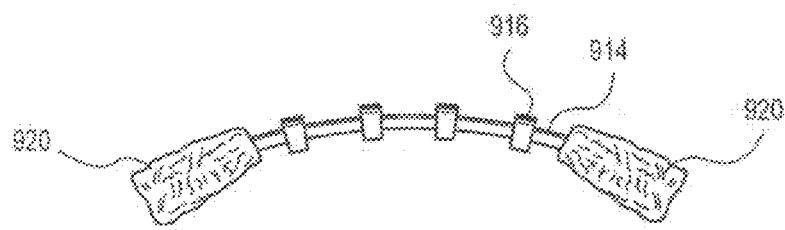
Figure 10C:
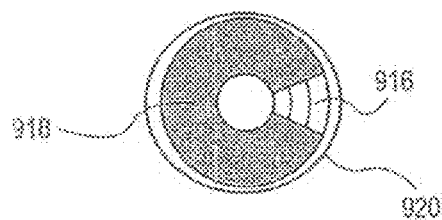
Figure 11A:
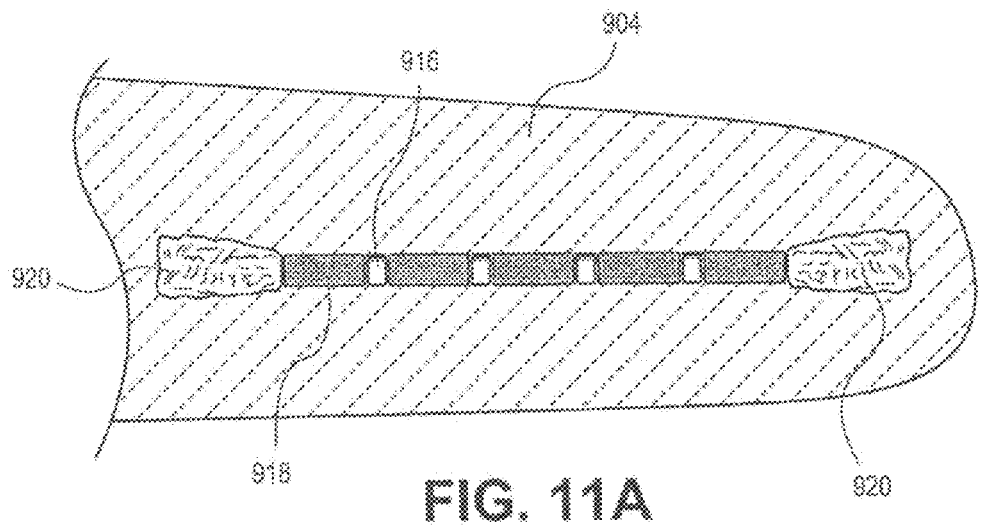
FIGS. 11A-B show details of the device shown in FIGS. 9 and 10 in place in the soft palate.
Figure 11B:
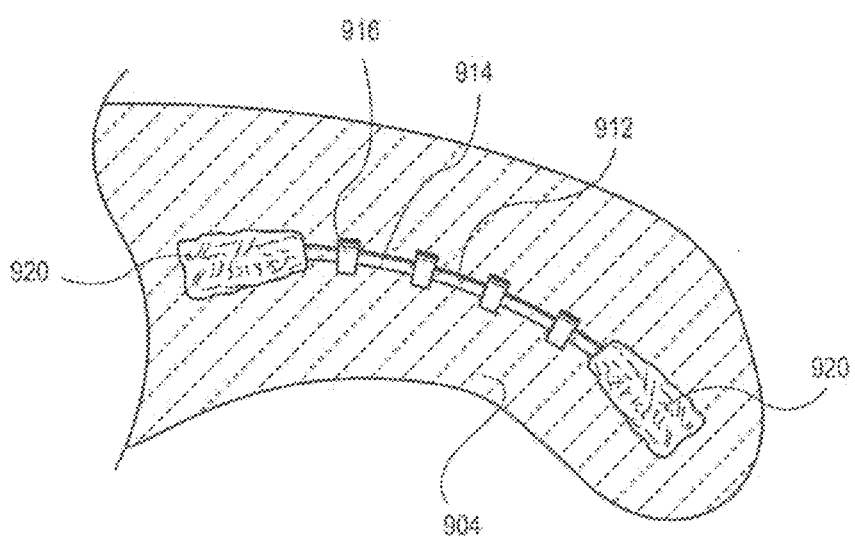

FIGS. 10A-C and 11A-B show more details of an airway-maintaining device 910 suitable for implantation in the soft palate. The device's deformed shape is shown in FIGS. 10A and 11A. In this shape, spacers 918 formed from a bioerodable material are disposed in narrow regions 914 of body 912 between wide regions 914 of body 912. Body 912 is formed from a resiliently deformable material (such as, e.g., silicone rubber, polyurethanes or other resiliently deformable polymer or a coil of stainless steel, spring steel, or superelastic nickel-titanium alloy or other resiliently deformable metal, or a composite of the resiliently deformable polymer and metal) and is deformed into the straight and elongated form shown in FIGS. 10A and 11A. The shorter and more curved at-rest shape of body 912 is shown in FIG. 10B. This is the shape the device will attempt to return to after the bioerodable portions 916 bioerode, thereby exerting force on the airway-forming tissue of the soft palate, as shown in FIG. 11B. In this embodiment, anchors 920 are formed from a non-woven fabric (such as polypropylene or polyester) to promote tissue ingrowth. Other anchors may be used, as desired. In this embodiment, the spacers 918 are injection molded from polycaprolactone, polylactic acid, polyglycolic acid, polylactide coglycolide, polyglactin, poly-L-lactide and have a C shape, although other manufacturing techniques (e.g., dipping processes for applying the spacers over the resiliently deformable polymer or metal), materials, and other shapes may be used as desired.

Figure 12A:
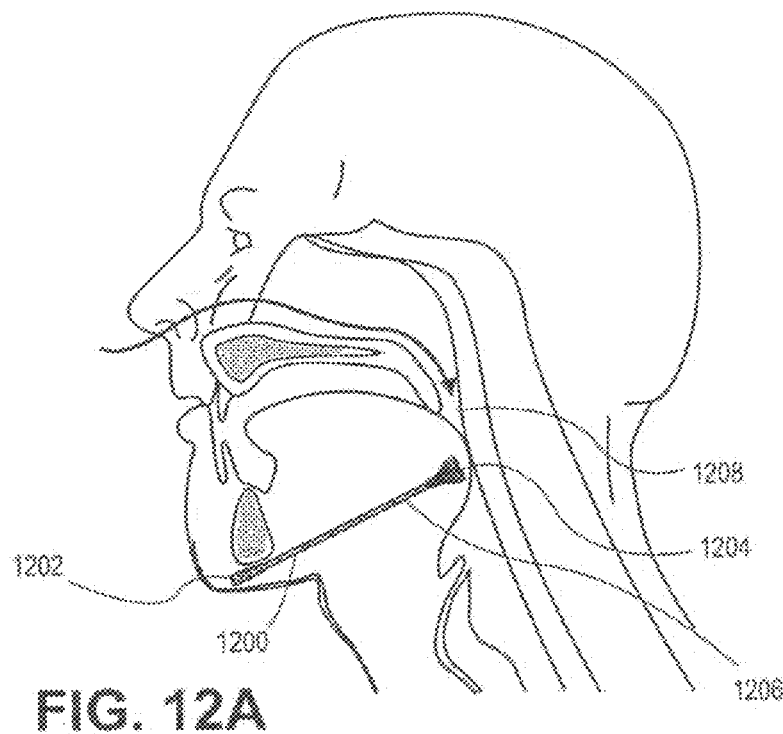
FIGS. 12A-B show an airway maintaining device according to yet another embodiment of the invention in place in the patient.
Figure 12B:
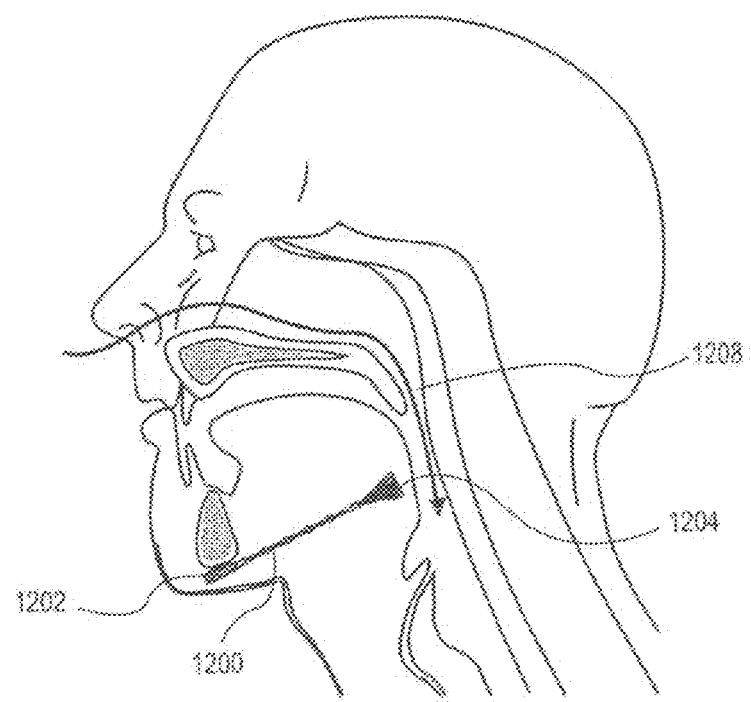

FIGS. 12A-B show another embodiment of an airway maintaining device 1200 implanted submandibularly into tongue tissue 1201 forming part of the patient's airway. Device 1200 has anchors 1202 and 1204 which differ from each other. Anchor 1204 is an expandable anchor, such as the self-expandable anchor 649 described above with respect to FIG. 6I, whereas anchor 1202 is not expandable. As shown in FIG. 12A, device 1200 when implanted into tissue 1201 is in an elongated deformed shape. Over time, bioerodable portions 1206 of device 1200 will bioerode, and device 1200 will attempt to return to its shorter at-rest shape, thereby exerting a force on tissue 1201 to maintain the patency of airway 1208, as shown in FIG. 12B.

Figure 13:
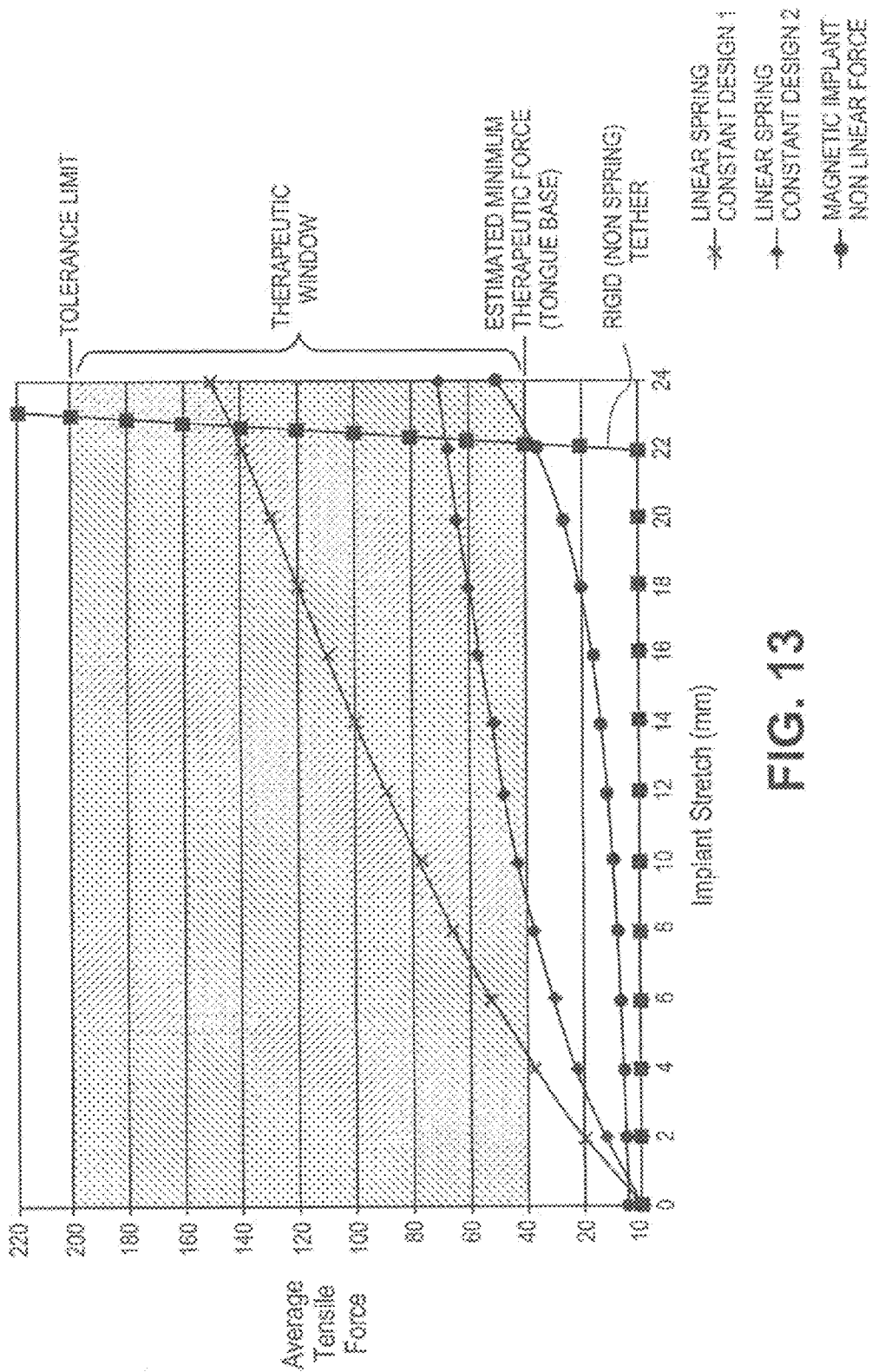
FIG. 13 is a graph comparing tensile force applied by embodiments of the invention and theoretical force applied by other obstructive sleep apnea therapy devices.
Figure 14A:
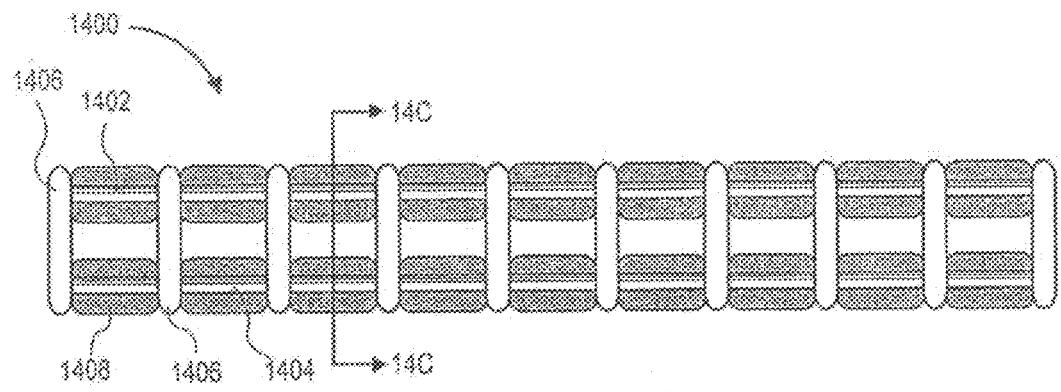
FIGS. 14A-C show an airway-maintaining device according to still another embodiment of the invention.
Figure 14B:
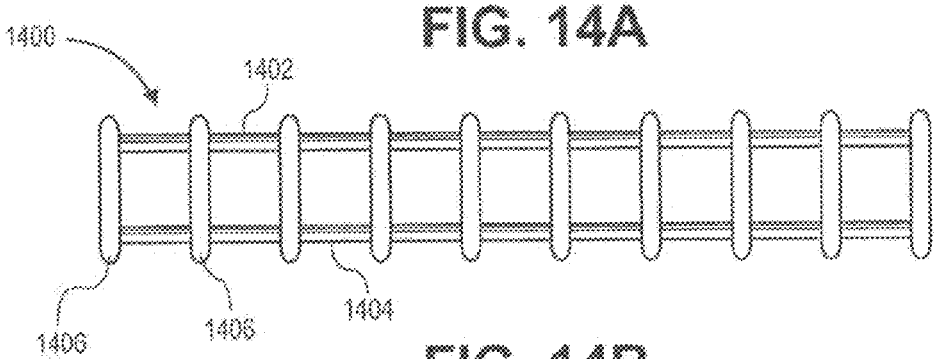
Figure 14C:
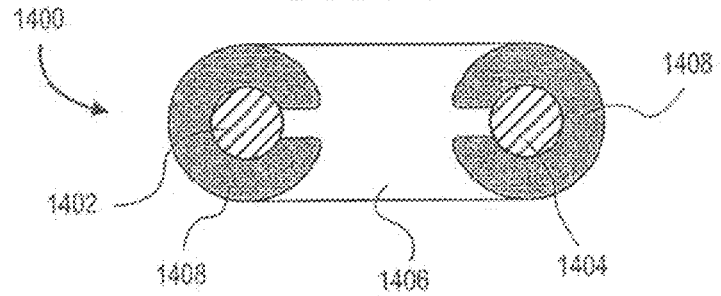

FIG. 13 is a graph comparing theoretical average tensile force provided to patient airway-forming tissue by various implantable obstructive sleep apnea therapy devices respect to the amount of stretching experienced by the implant. Tether devices are shown by the two lines formed by the square data points. As can be seen, such rigid devices provide no tensile force on the patient's tissue until all slack has been removed, at which point the tether provides a nearly infinite force, possibly exceeding the patient's tolerance limit.

The curve formed by the round data points show theoretical tensile force applied by magnet-based obstructive sleep apnea implants. As can be seen, such devices have a very narrow operational range falling with the therapeutic range providing a benefit to the patient through the application of a minimum therapeutic force.

The curves formed by the diamond and cross data points show theoretical tensile forces applied by two airway-maintaining devices according to this invention having two different spring constants in their deformable device bodies. As shown, these devices can be designed so that they provide beneficial airway maintenance therapy to the patient over a wide range of lengths.

Figure 15A:
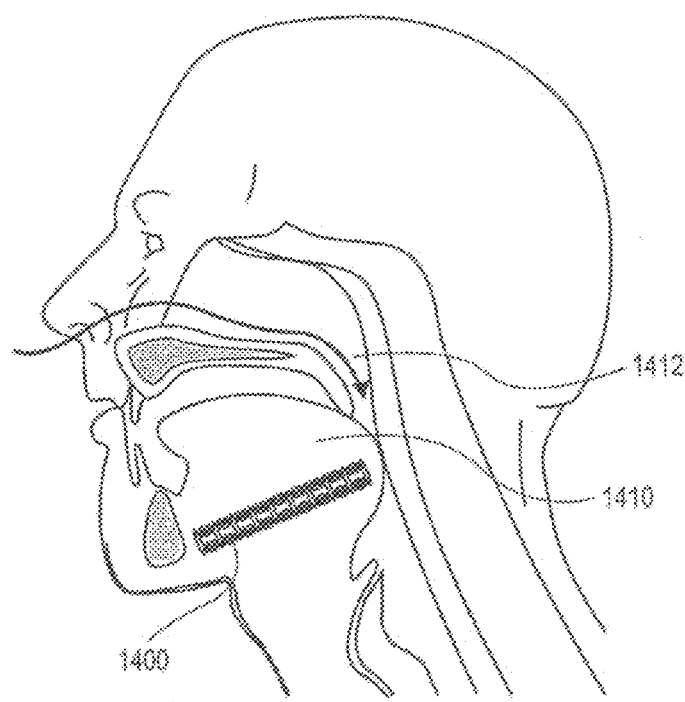
FIGS. 15A-B show the device of FIG. 14 in place in patient.
Figure 15B:
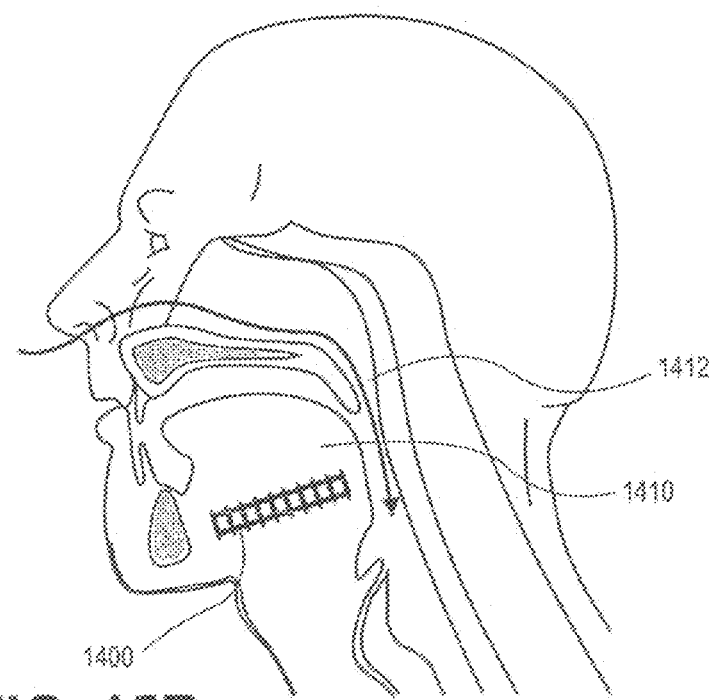

FIGS. 14A-C and 15A-B show yet another embodiment of the invention. Device 1400 has a device body with two elongate rails 1402 and 1404 formed from a resiliently deformable material, such as silicone rubber. A plurality of spaced-apart oval flanges 1406 are attached to rails 1402 and 1404. In the deformed state shown in FIGS. 14A and 15A, C-shaped bioerodable spacers 1408 are disposed between adjacent flanges 1406 to maintain the device in its elongated shape. When spacers 1408 bioerode over time, device 1400 moves toward the at-rest shape shown in FIG. 14B, thereby exerting a force on the patient's airway forming tissue (shown as the tongue 1410 in FIG. 15) to maintain patency of the airway 1412 as shown in FIG. 15B.

Figure 16A:
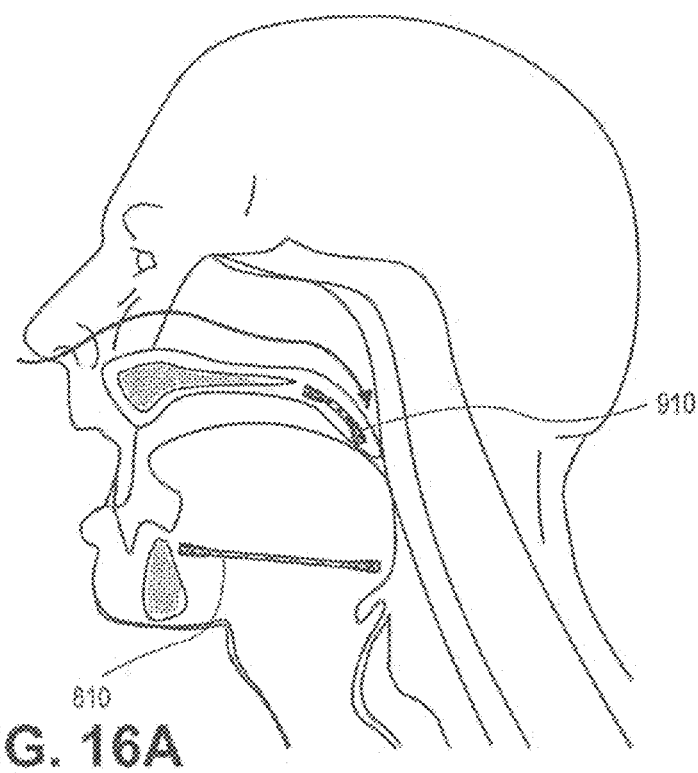
FIGS. 16A-B show the devices of FIGS. 8 and 9 in place in a patient.
Figure 16B:
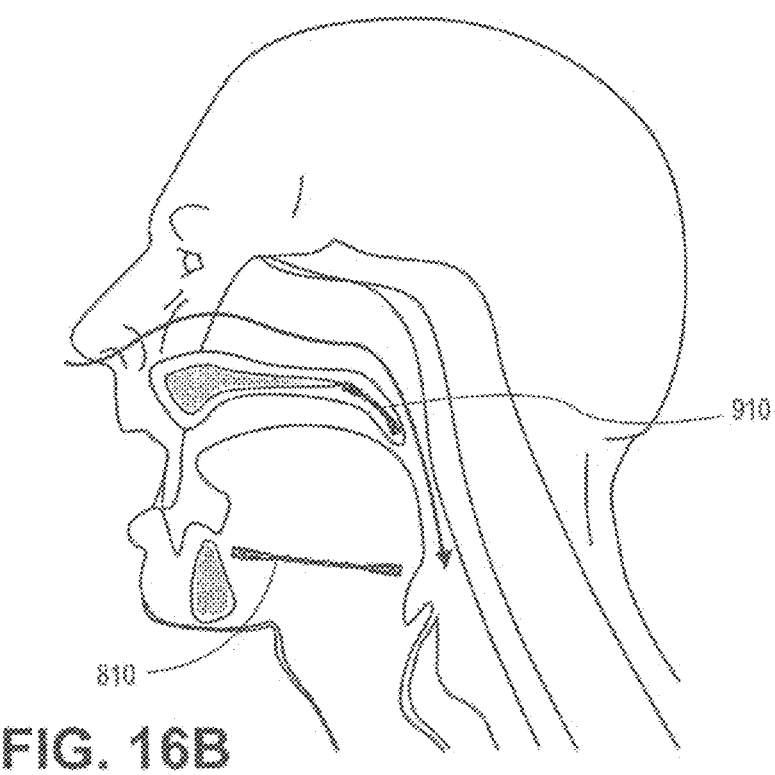

FIGS. 16A-B demonstrate how multiple airway-maintaining devices may be implanted into a single patient, such as the tongue device 810 and the soft palate device 910 described with respect to FIGS. 8 and 9 above, respectively.

Figure 17A:
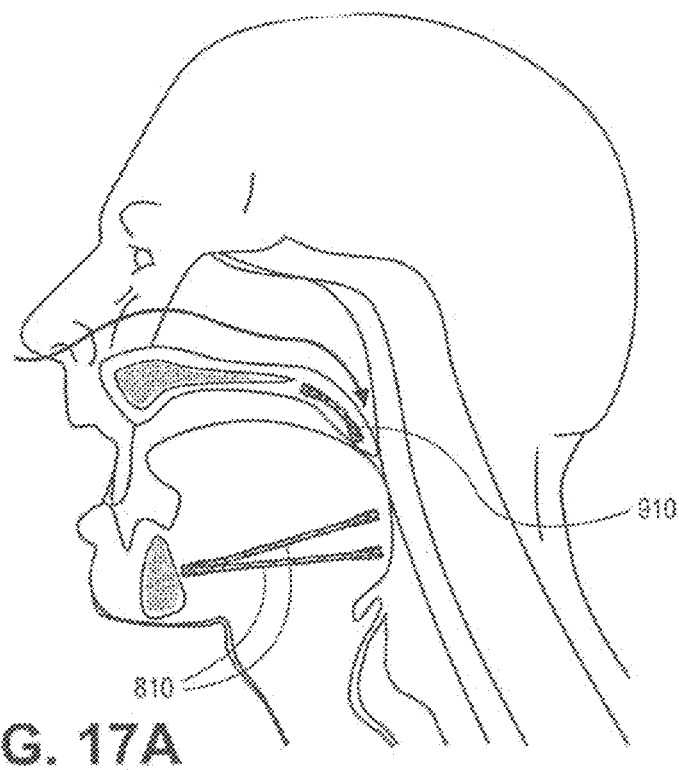
FIGS. 17A-C show multiple devices of FIGS. 8 and 9 in place in a patient.
Figure 17B:
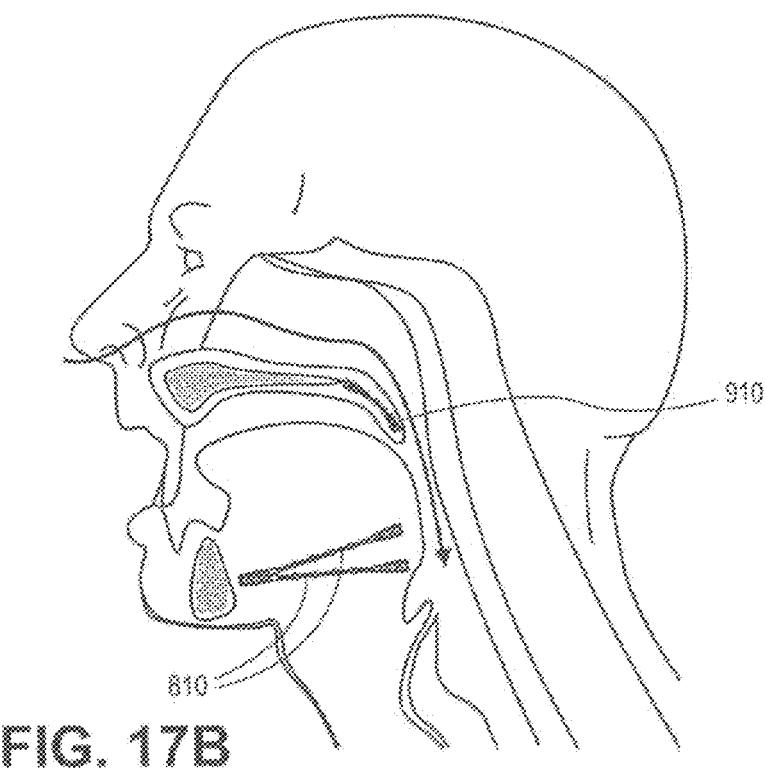
Figure 17C:
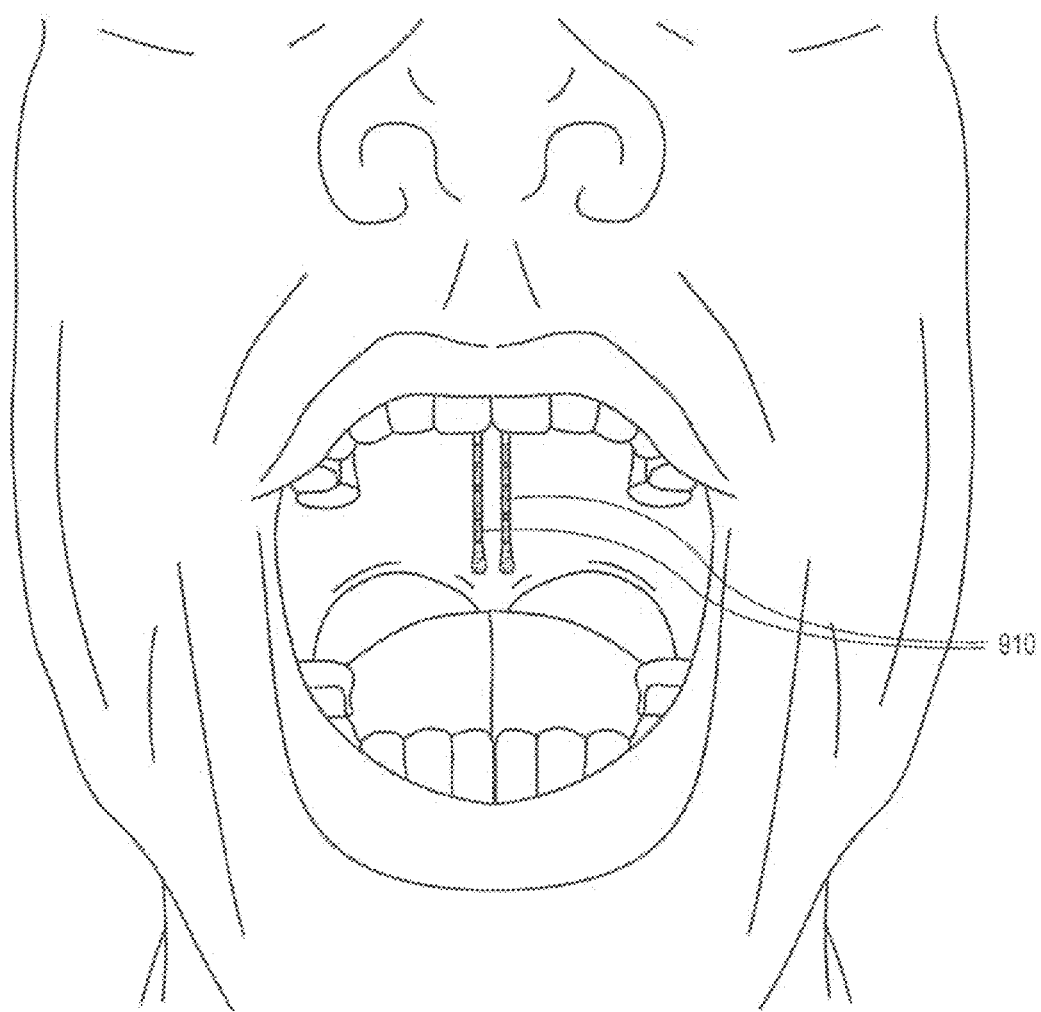

Likewise, FIGS. 17A-C show how multiple airway-maintaining devices may be implanted into the same region of airway-forming tissue.

Figure 18A:
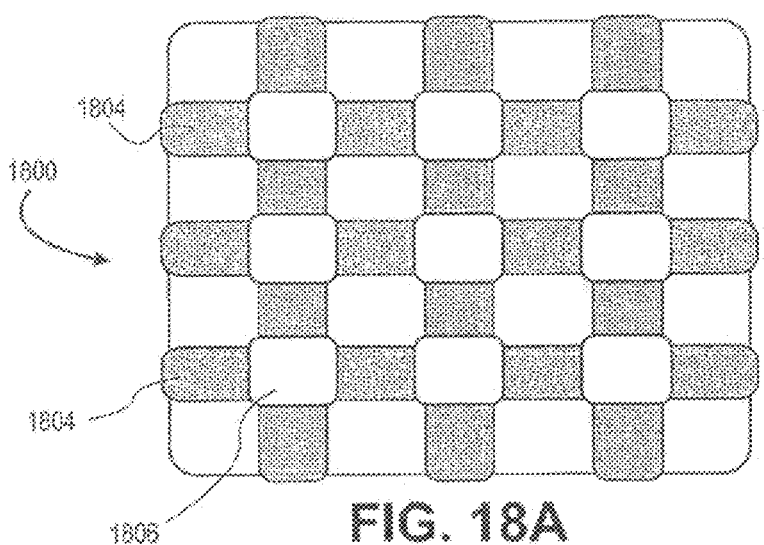
FIGS. 18A-C show another embodiment of the airway maintaining device of this invention.
Figure 18B:
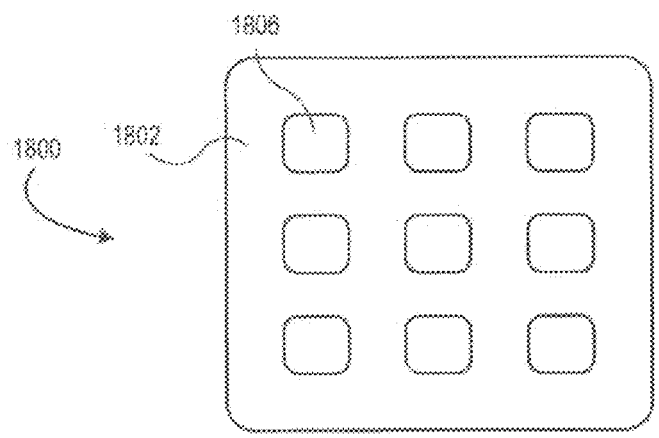
Figure 18C:
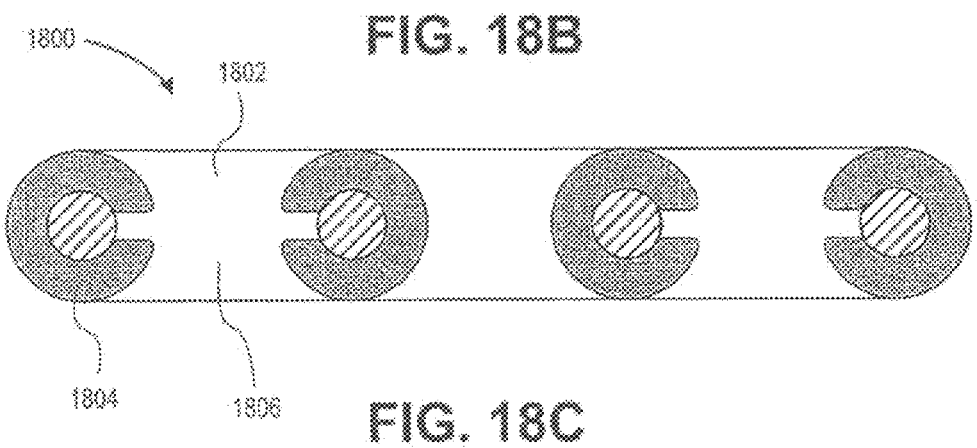

FIGS. 18 A-C show an embodiment of an airway-maintaining device 1800 in which the deformed state of the device body 1802 shown in FIG. 18A is both longer and wider than the at-rest state of the device body 1802 shown in FIG. 18B. Bioerodable spacers 1802 are disposed in openings 1804 formed in resiliently deformable body 1802. As the spacers erode, the body 1802 will move toward its at-rest shape. The openings in the deformed and at rest shapes 1804 and 1806 constitute anchoring elements. This embodiment could be placed in an anatomical structure such as the soft palate and could exert force on the airway forming tissue in two directions to maintain patency.

In some embodiments, the device may include one or more bioactive agents in the bioerodable portion(s). Bioactive agents such as drugs or hormones that are eluted during the course of erosion of the bioerodable materials, may serve, for example, to promote healing of the implant wound, or to promote stabilization of the implanted device within the tissue site by, for example, promoting the toughening the fibrotic tissue capsule that forms around the implanted device.

FIGS. 19A-D show an embodiment of the invention similar to the devices shown in FIGS. 6A-J with long term elongate implant portion 114 shown without a bioerodable material portion (FIGS. 19 C-D) and implant system 100 shown with bioerodable portion 110 at least partially enveloping the long term elongate implant portion of the device (FIGS. 19 A-B). In this example, the bioerodable portion is helically wound around the elongate implant. Bioerodable portions 110 are adjacent or connected with wide sections 108 of the long-term implant and may be configured to resist a compressive force from the long term implant or to apply an expansive force to the long term implant. The long term implant may be made of a resiliently deformable material, such as a silicone material (e.g. silicone rubber), polyurethane or other resiliently deformable polymer or a coil of stainless steel, spring steel, or superelastic nickel-titanium alloy or other resiliently deformable metal, or a composite of the resiliently deformable polymer and metal. In particular, when placed in an animal's body, one or more bioerodable portions 110 may hold the elongate implant in a first, elongated shape until the implant is anchored to an airway tissue, such as by a fibrotic response or tissue growth through one or more holes 106 in anchor end(s) 104. Over time, the bioerodable material bioerodes, the device shortens and exerts a therapeutic force on airway tissue. Compare the relative compositions, shapes, and lengths of foreshortened device 114 (FIGS. 19C-D), having exposed narrow sections 116 after bioerosion, with device 100 (FIGS. 19A-B) before substantial bioerosion has taken place and having bioerodable material 110 partially enveloping the long-term implant.

Figure 19A:
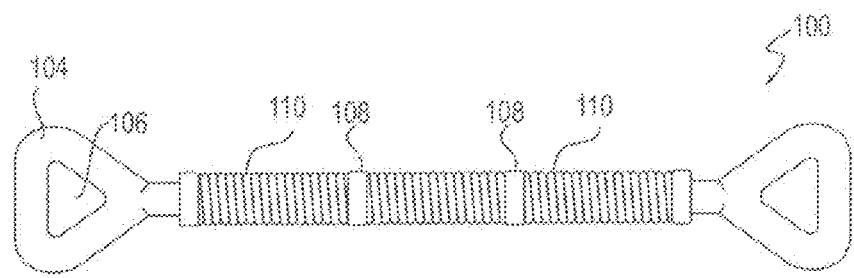
FIGS. 19 A-B show two views of an embodiment of a device or implant system with a bioerodable material around an elongate long-term implant.
Figure 19C:
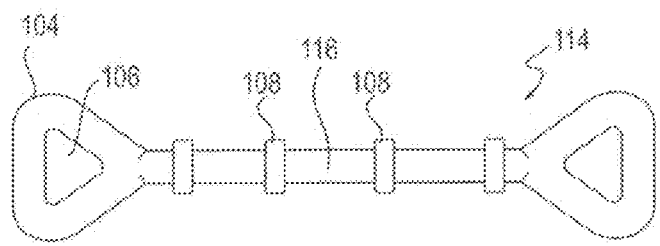
Figure 19B:
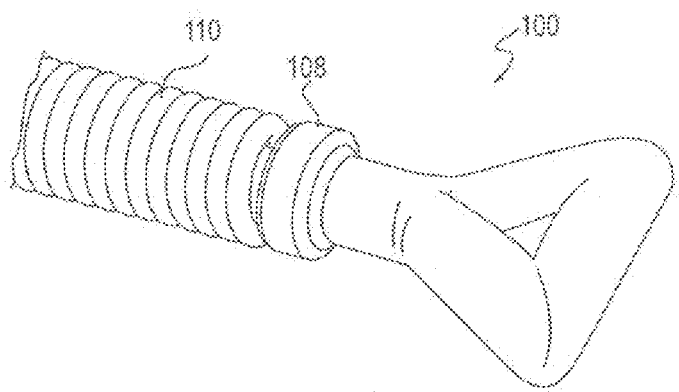
Figure 19D:
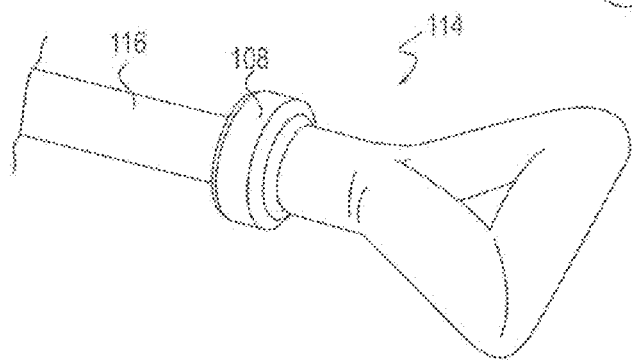
Figure 20A:
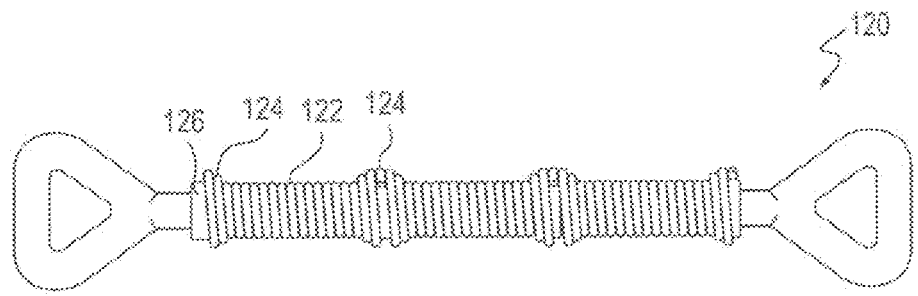
FIGS. 20A-B show two views of a device that has prematurely foreshortened.
Figure 20B:
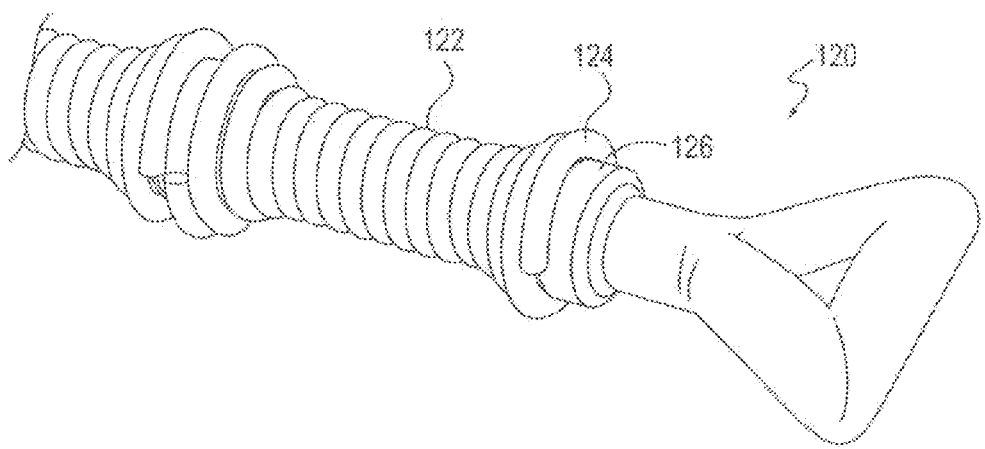

It may be beneficial for a device to remain in an elongated shape until substantial or sufficient tissue growth has taken place and the ends of the device are anchored into airway tissue. However, in some conditions a device might not maintain a sufficiently elongated, (stretched) configuration as shown in FIGS. 19A-B for a period of time sufficient to allow tissue to anchor the implant into tissue (e.g. to anchor the implant so that it can exert a desired therapeutic force on the tissue). Rather, if the implant shortens too much from its first, elongated shape before becoming anchored in tissue (or does not become anchored), it may not be capable of exerting sufficient force on airway tissue to have a therapeutic effect. Some specific devices, similar to those shown in FIGS. 19 A-B, when tested in an animal model, did not exhibit the desired tissue effect. It is hypothesized that normal airway tissue movement imposed mechanical forces on the devices that led to premature device foreshortening. See Example 2. In particular, in vitro testing showed that one explanation for the lack of the desired tissue effect could be premature long-term implant foreshortening due to mechanical agitation causing its premature release from the bioerodable material that otherwise holds it in an elongated configuration (shape). When implant systems were subject to ultrasound vibration in a saline bath (to model or mimic the implant environment in a body), coiled bioerodable material, such as that shown in FIGS. 19A-B, unwound relative to the long-term implant axis. See Example 2. FIGS. 20 A-B show an example of an implant, such as the one depicted in FIGS. 19A-B, in which coils including end coil 124 at an end of bioerodable helix 122 on device 120 have unwound and part of wide section 126 of the long term implant has retracted inside the end coils. The coils remaining wound around the narrow long term implant portion may not be able to provide a sufficient resistive force to hold the long term implant in a desired, elongated configuration (shape). Therefore, it may sometimes be beneficial to create, reinforce or change a device structure such that it will substantially hold a desired shape in vivo for a sufficient period of time (e.g. in the presence of mechanical or other forces) to allow tissue anchoring of the device to take place. Either a bioerodable or a long term implant portion (or both) may be configured or altered to improve the ability of the long term implant to be placed and to remain in a tensioned shape (e.g. held by the bioerodable portion) until sufficient tissue growth has taken place. An initial tensioned shape or configuration may be any shape or configuration that creates a tension between a bioerodable material and a long-term implant that is different from a final shape or configuration (in which the bioerodable material has bioeroded and no longer exerts a tension on the long term implant). Alternatively, an additional piece (such as a holder or clip) may hold the bioerodable portion or long term implant in a preferred shape or configuration.

In some embodiments, an implant system according to the disclosure includes a resilient elongate implant body having a first insertion shape and a second therapeutic shape and a bioerodable material including at least two coils that at least partially envelop the resilient elongate implant body, wherein the coils are coupled together to form a coupled coil structure. A therapeutic shape of an elongate implant body may be a shape that the body takes after a bioerodable portion bioerodes. A therapeutic shape may be a shape configured to exert a desired force) on a target tissue (e.g. an airway forming tissue).

A bioerodable portion may be manufactured to better maintain an initial or desired shape, for example, by changing the way the bioerodable material is otherwise held in place relative to the resilient or elongate long term implant. The bioerodable portion may be held in position along the elongate implant in any way. For example, the portion may be held using a chemical coupling and/or using a mechanical coupling (e.g. an interlocking). To aid in device performance, including maintaining a device shape, portions of the bioerodable implant may be made less flexible compared with other, more flexible sections. The less flexible portions may hold the implant in a first shape and prevent the bioerodable portion from undergoing undesired movement (e.g. unwinding) relative to the long term implant. A point on an implant may be made less flexible, for example, by coupling one portion of a bioerodable material to another portion of the bioerodable material (e.g. coupling to itself). In one embodiment, two points on the bioerodable portion may be fused together. The two points may be on the same coils or may be on different coils. FIG. 21 shows two coils on bioerodable helix 132 of implant 130 fused at fusion point or bridge 137 at a first end to bridge a first region. The bridge may create a region of lesser flexibility on the bioerodable portion, reducing movement of the bioerodable implant, and thereby maintaining the bioerodable material in an enveloping configuration relative to the long term implant. A point connecting a coil and a bridge has lesser flexibility than a flexibility of a (or either) coil to which it is coupled. Any number (or no) bridges may be made on a bioerodable portion. A bridge may have a different flexibility.

Figure 21A:
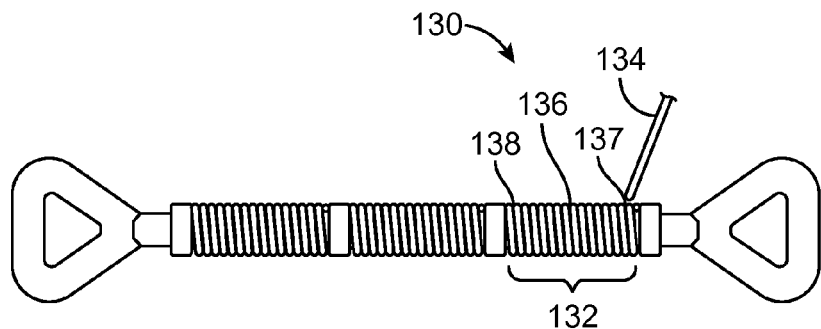
FIGS. 21A-B show a method of coupling a bioerodable material to itself to form a bridge according to one aspect of the invention.
Figure 21B:
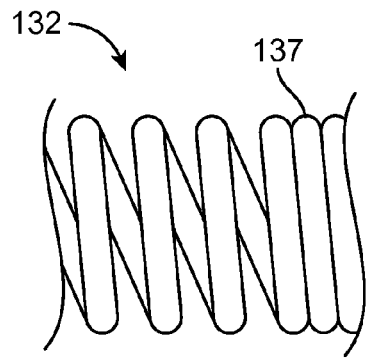

A bioerodable portion may be manufactured to better maintain an initial or desired shape, for example, by changing the way the bioerodable material is otherwise held in place relative to the resilient or elongate long term implant. The bioerodable portion may be held in position along the elongate implant in any way. For example, the portion may be held using a chemical coupling and/or using a mechanical coupling (e.g. an interlocking). To aid in device performance, including maintaining a device shape, portions of the bioerodable implant may be made less flexible compared with other, more flexible sections. The less flexible portions may hold the implant in a first shape and prevent the bioerodable portion from undergoing undesired movement (e.g. unwinding) relative to the long term implant. A point on an implant may be made less flexible, for example, by coupling one portion of a bioerodable material to another portion of the bioerodable material (e.g. coupling to itself). In one embodiment, two points on the bioerodable portion may be fused together. The two points may be on the same coils or may be on different coils. FIG. 21A shows two coils on bioerodable helix 132 of implant 130 fused at fusion point or bridge 137 at a first end to bridge a first region. FIG. 21B depicts a portion of the helix 132 alone, without the implant, in an expanded configuration. This view is to highlight the difference between the bridged coils at bridges 137, 138 and the other coils on the helix 132. The bridge may create a region of lesser flexibility on the bioerodable portion, reducing movement of the bioerodable implant, and thereby maintaining the bioerodable material in an enveloping configuration relative to the long term implant. A point connecting a coil and a bridge has lesser flexibility than a flexibility of a (or either) coil to which it is coupled. Any number (or no) bridges may be made on a bioerodable portion. A bridge may have a different flexibility.

In some embodiments, coils may be fused at both ends of a bioerodable portion. FIG. 21 shows two coils fused at a first bridge 137 and a second bridge 138 at a second end of the bioerodable portion. Fusing or anchoring both ends of a bioerodable portion may prevent a bioerodable implant from rotating or unwinding relative to the long term implant.

In another embodiment, two other coils may be fused to form a third bridge 136. The third bridge may be anywhere along the bioerodable portion, but in one particular example it is near the middle of a bioerodable portion. The third bridge may, for example, provide additional strength to the bioerodable portion to resist movement caused by mechanical agitation from airway tissue movement and may serve as a backup in the event that one of the first two bridges near an end of the bioerodable portion prematurely breaks while implanted (e.g. breaks before tissue growth has anchored the implant) such that the breakage might otherwise allow the bioerodable portion to unwind and the long term implant portion to prematurely foreshorten. A fourth, fifth, sixth, seventh, eighth or more bridges may be formed. In some embodiments, there may be a bridge at least every 1 mm, every 2 mm, every 3 mm, every 4 mm, every 5 mm, every 10 mm, or every 15 mm. In some embodiments, each coil may be fused to at least one (or at least two) other coil(s). In some embodiments, each coil may be linked to at least one other coil, forming a plurality of bridges. In one particular embodiment, all of the coils are fused together. An implant may have one, two, three or more than three separate bioerodable portions. Any (some, or all) of a bioerodable portion(s) may be fused to itself or one (or more) bioerodable portion(s) may be fused to one or more other bioerodable portion(s).

The bioerodable material may be linked or fused to itself in any way. The points on the material may be fused using a source that can generate energy (heat). The energy (heat) may melt a portion of the bioerodable material to cause it to bind to another portion of the bioerodable material and remain bound after cooling. The heat source may be a direct heat source (such as a soldering iron) that is at a temperature higher than an implant temperature or the heat source may be an indirect source such as a chemical source or light source, vibrational welding, induction welding, ultrasonic welding, or radiofrequency welding source that causes heat to be generated in the implant.

Figure 22A:
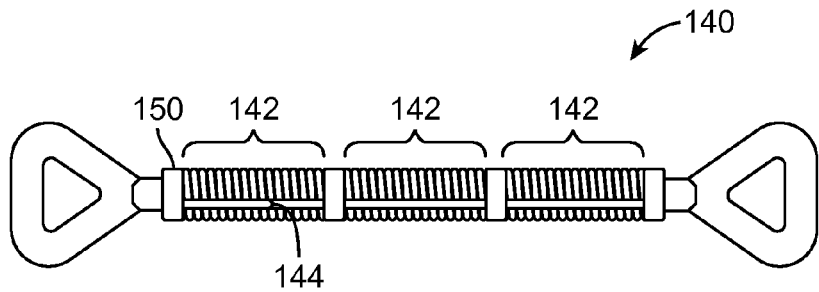
FIGS. 22 A-C show two versions of a device with (FIGS. 22 A-B) and without (FIG. 22 C) coupling.
Figure 22B:
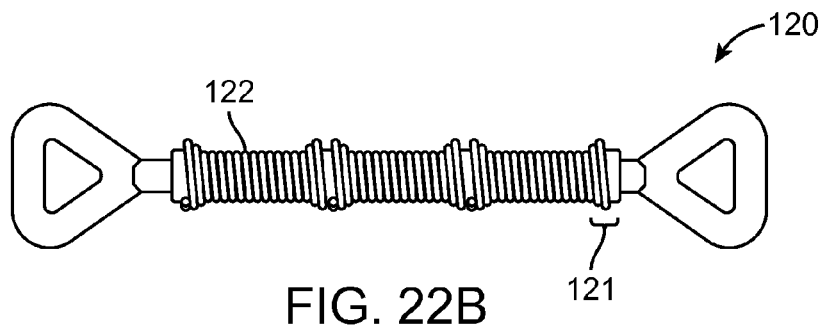

Instead, or in addition to a bioerodable material melting or otherwise linking to itself, a bioerodable material may be coupled to itself using an additional joining material such as an adhesive that bonds or a solvent that bonds by melting adjacent surfaces together or small clip or mechanical attachment to form a bridge and couple two (or more) points on the material. FIGS. 22A, C show implant 140 with bioerodable material in the form of helix 142. Bar (or bridge) 144 connects essentially all of the coils of a bioerodable portion, creating a support strut that may help hold the helix in an initial shape. The support strut may create a point(s) or region(s) of reduced flexibility on the helix and the helix may then resist movement from airway tissue and therefore maintain an elongated shape until tissue growth has anchored the implant (e.g. to create a biological anchor). An end of the helix opposes wide section 150 of the long term implant to thereby hold the long term implant in an elongated configuration. Compare the coils of the helix and the relative length of implant 140 with bar 144 in place along the coils in FIGS. 22 A, C with a foreshortened bioerodable helix, the unwound coils 121 and relative length of implant 120 without a support strut shown in FIG. 22B. The bioerodable portion in implant 120 did not resist a compressive force from the long term implant, and the long term implant prematurely shortened. A bar may connect essentially all of the coils of a helical portion together, as shown in FIG. 22A, C. Additionally, a second (or more than two) bar(s) may be placed along the helix to create additional regions of reduced flexibility, provide additional support, and reduce relative rotational movement of the helix.

Figure 22C:
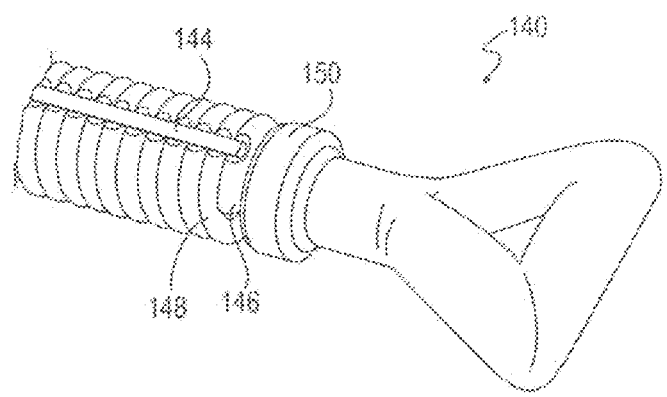

Although any two (or more) coils may be connected by a bar, it may be especially useful to couple end coils, such as coils 146, 148, as shown in FIG. 22C to prevent rotation of the helix around the axis while maintaining device flexibility. In some embodiments, a first bar may be placed at a first end of a helix to connect a first set of end coils, and a second bar may be placed at a second end of a helix to connect a second set of end coils. In another embodiment, an additional bar(s) may be placed along two non-end coils to provide additional support, such as for backup in case one of the end bars breaks prematurely.

A support structure between two (or more) portions of a bioerodable material may be any material that provides support (e.g. creates regions of lesser flexibility) and may be any shape (e.g. a cylinder, a sphere, a straight bar, a wavy bar, a serpentine ribbon, etc.). A bar or other joining or support material may be connected with the bioerodable material using any means (e.g. heat or mechanical). The additional joining material may be the same material as the bioerodable portion or may be a different material.

Figure 23A:
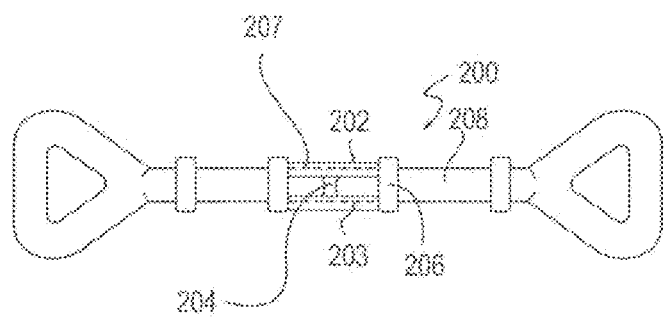
FIG. 23 A, B shows two views of a device with cuff or C-shaped portion partially enveloping a long term implant portion and connected by a bridge.
Figure 23B:
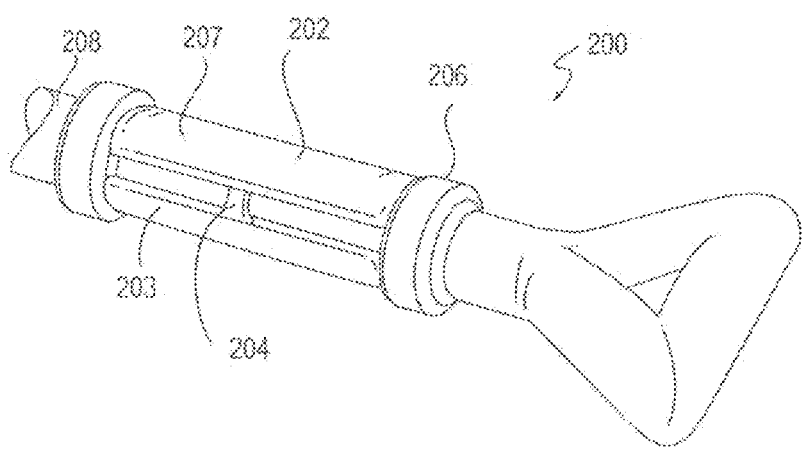

A bioerodable material that is coupled to itself may be any shape that is able to maintain a shape of the long term implant and/or resist a compressive force (or maintain a tensioned force) from the long term implant. As shown in implant system 200 in FIG. 23 A, B, additional joining material 204 may couple two long sides 202, 203 of C-shaped or cuff shaped material 207 to hold long-term elongate implant 208 in an elongated position. A C-shaped or cuff shaped material may be easy to manufacture and may be easy to place (e.g. snap) over an elongated implant, and the additional joining material may hold the C-shaped material in place (e.g. prevent the cuff from falling off the elongated implant) so that it is able to resist a compressive force from wide section 206 to thereby place or hold long term implant 208 in an elongated shape. Although shown as a continuous material, a C-shaped bioerodable material may have any number of holes or open spaces. Holes or open spaces may improve device flexibility prior to bioerosion compared with a solid structure, and/or may allow better penetration of a body fluid. This may allow better timing of device erosion which in turn may influence both device anchoring and device function. In some embodiments, a bioerodable structure may be essentially a cylindrical structure that envelops an axis or envelopes part of an axis of a long term implant portion. A cylindrical structure (e.g. an open ended tube) may be continuous or may include open spaces (e.g. holes, slots). A bioerodable implant described herein, including a cylindrically shaped bioerodable implant, may be made by any means and may be connected with a long term implant using any methods or any means. In some embodiments, a portion of a bioerodable implant may be placed over a long term implant and then fastened in place (e.g. In FIG. 23, joining material 204 in FIGS. 23 A-B may extend along the length of sides 202, 203 to form a cylindrical structure. Alternatively, a bioerodable implant may be manufactured as an extruded tube or may be formed using a mold, and after forming may be placed over the long term implant.

Any method or structure that allows the bioerodable portion to maintain a long term implant in a desired shape for a desired period of time may be used. A bioerodable material may be coupled to itself using a mechanical joining to hold two (or more) portions of bioerodable material together. Any form of mechanical joining may be used (e.g. forming a crimp, mating complementary portions together).

Figure 24:
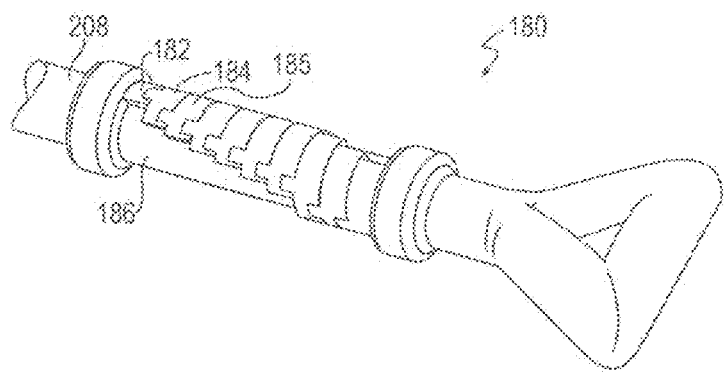
FIG. 24 shows an implant system with a modular design.

In one embodiment, a bioerodable portion may be coupled with one or more other bioerodable portions. Two C-shaped bioerodable pieces, each of which wraps partially around an axis (e.g. a long term implant portion) may be coupled (e.g. bridged) to one another. More than two (e.g. a series) of C-shaped or other shaped bioerodable pieces may be coupled together as shown in FIG. 24 to form system 180 with a modular, mechanically interlocking bioerodable portion around long term implant 208. Each piece may wrap a short distance (e.g. about a quarter of the way), halfway, or more than halfway (e.g. three-quarters of the way to form a C shape or all the way) around an axis, such as an elongate long term implant axis. The pieces may have any conformation and may have features (e.g. snap fit, lock and key) to lock two or more than two pieces together and/or to lock or otherwise connect a piece with a long term implant portion. In one embodiment, the C-shaped (or other shaped) bioerodable pieces may be lined up (e.g. to substantially form a cuff shape that is open along one side similar to the cuff in FIG. 23 A, B) or bioerodable portions 182, 184, 185 may be offset from one another relative to an elongate axis as shown in FIG. 24. Offset shapes may provide ease of assembly and/or may provide better (overall or local) implant flexibility, due to the presence of an open space, such as space 186 configured to allow implant bending. Having a space, such as space 186, may also minimize an amount of biodegradable material present in a device, which may in turn minimize or prevent a side effect (such as inflammation) after a device system has been implanted in a body and the bioerodable portion has bioeroded.

One aspect of the invention provides a method of manufacturing a bioerodable implant including the steps of wrapping a bioerodable material at least partway around an axis to create a wound bioerodable implant, the bioerodable implant having two points, and coupling the two points to each other. See, for example, FIG. 21. Any biocompatible, bioerodable material can be used, including any described elsewhere in this application or known in the art.

Another aspect of the invention provides a method of manufacturing an implant system, the implant having an elongate (or resilient) implant body and a bioerodable support material configured to hold the elongate (or resilient) implant body in a first, elongate shape, including the steps of wrapping the bioerodable support material at least partway around the implant body, the bioerodable support material having two points on it, and coupling the two points with each other to create a coupled bioerodable support material.

In one embodiment, a thin strand of a polymer may be wrapped around an axis to create a helix and the helix may be coupled to itself. In one embodiment, a polymer may be based on lactic acid and/or glycolic (e.g. poly(lactic acid) or poly(DL-lactic-co-glycolic acid)) or any of the materials listed above or known in the art. The method may further include applying an expansive force to the elongate long term implant with the bioerodable material to thereby place or hold the long term implant in an initial shape, as shown in FIG. 21. A coupling step may include attaching (e.g. by applying an adhesive, by applying an other chemical (such as a polymer initiator), or by supplying an energy source) to two points on a bioerodable material to create a support strut. FIG. 21 shows applicator 134 applying an activator (e.g. an adhesive, another chemical or an energy) to thereby fuse two points on the bioerodable material. Coupling the bioerodable may include heating the bioerodable material to melt the two points together. A bioerodable material may additionally (or instead) be coupled with a long term implant portion.

Another aspect of the invention provides a method of manufacturing an implant system, the implant having an elongate, resilient, long term implant body and a bioerodable (support) material configured to hold the resilient implant body in a first, elongate shape, the method including the steps of wrapping the bioerodable support material at least partway around the implant body (or at least partially enveloping the elongate implant body with a bioerodable support material), the bioerodable support material having two points on it; and coupling the two points with each other to create a coupled bioerodable support material.

Figure 25:
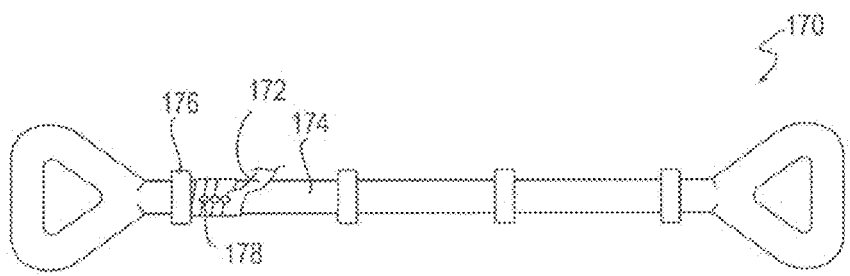
FIG. 25 shows a ribbon-like structure wrapped around a long term implant and coupled to itself.
Figure 26:
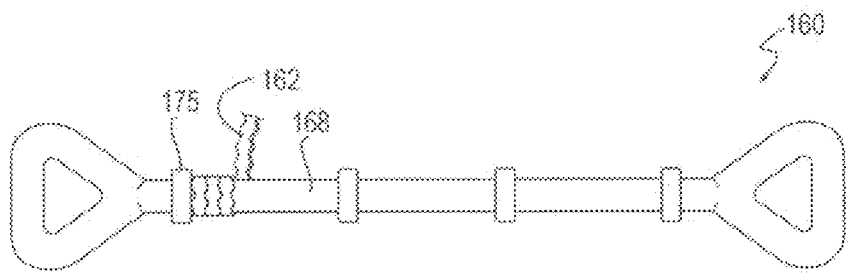
FIG. 26 shows an embodiment of a device with a self-linking bioerodable portion.

In one embodiment, a ribbon like bioerodable material 172 is wrapped at least partway around axis 174, as shown in FIG. 25. The ribbon may overlap on itself. Two points on the ribbon-like material may be coupled to create a first bridge 178 which has less flexibility than other points on the ribbon-like material. The bridge may be created by chemically joining two loops of the ribbon, by adding a new (bioerodable) structure between the two loops, or by mechanically interlocking the loops. Other bridges may be made between other loops of the ribbon-like material. In other embodiments, each loop may be coupled with one (or more than one) other loop(s). An end of the ribbon may abut wide region 176 of the long term implant to thereby place (and/or hold) implant 170 into a first shape. The ribbon-like material may have smooth edges or may have shaped edges. Shaped edges may be configured to couple, or mechanically connect (e.g. interlock). FIG. 26 shows implant 160 with ribbon-like material 162 being wound around long term implant 168. Adjacent sections of ribbon-like material may mate to hold ribbon-like material 162 in place. Any features that are able to hold the ribbon-like material together (and/or prevent it from unwinding relative to the long term implant) can be used. For example, the features may be tongue and groove or lock and key. A ribbon-like material may provide an expansive force to a long term implant portion; for example to wide section 175.

Figure 27:
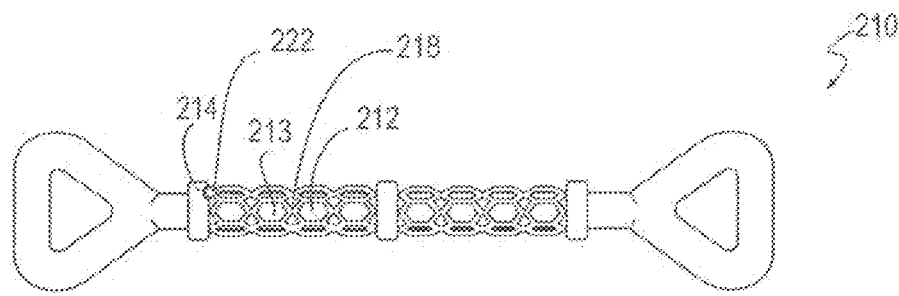
FIG. 27 shows an embodiment of a device with a stent-like structure holding the long term portion.

FIG. 27 shows another embodiment of an implant system with a bioerodable material configured to hold a long term implant in an initial or first shape. The bioerodable material may include a mesh or series of loops (e.g. a stent) that envelop or hold a long term implant to create implant system 210. The loops may wrap all the way around the long term implant or may wrap partially around. Loops 212, 213 may be coupled with each other to create bridge 218 of relatively lesser flexibility relative compared with the rest of the loop(s).

Alternatively, or additionally to being coupled to itself, the bioerodable material may be coupled with the long term implant. The bioerodable material may be coupled with the long term implant using any method or any material(s). The coupling may serve to hold the bioerodable material in a desired shape or configuration. A bioerodable material and a long term implant may be coupled using any chemical or mechanical means, including any described elsewhere in this application. As shown in FIG. 27, they may be coupled using corresponding mating structures 214, 222.

Figure 28:
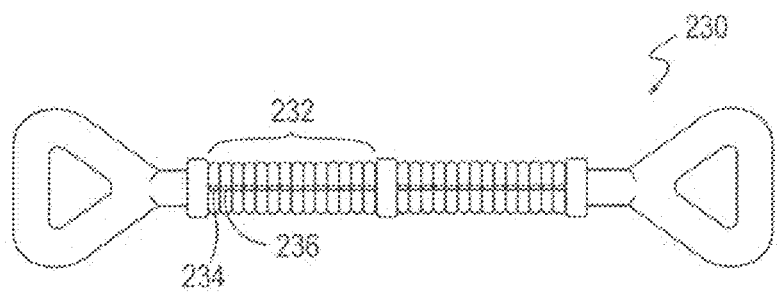
FIGS. 28 and 29 show embodiments of devices with regions of greater flexibility and regions of lesser flexibility.
Figure 29:
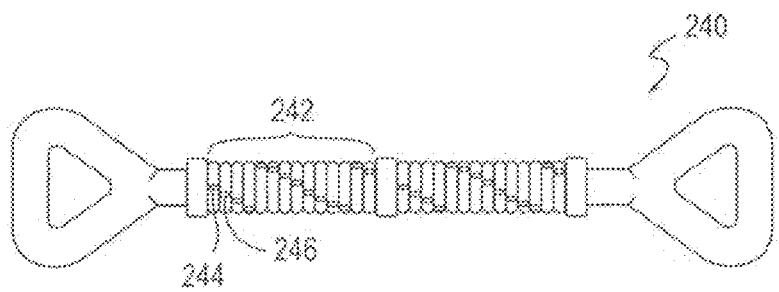

The bioerodable material may have regions of different flexibility. The regions may hold or help hold the bioerodable material (and the long-term elongate implant) in a preferred shape. FIGS. 28 and 29 show implants with bioerodable material having regions of differing flexibility. FIG. 28 shows implant system 230 with a bioerodable spring coiled around a long term implant. The coils of the spring have regions 234, 236 that are less flexible than other portions (the rest) of the coils of bioerodable portion 232. For example, these regions may be thicker, wider, or may include a different material with different resiliency (e.g. different flexibility). Any number of regions of lesser flexibility may be present on a coil. For example, each coil may have a second region of lesser flexibility on the coil (e.g. half-way around the coil) such that each coil has two regions of lesser flexibility (hinges) that control (e.g. prevents or reduces) a rotation or other movement of the coil. FIG. 29 shows implant 240, which is similar to the device shown in FIG. 28, but regions of lesser flexibility 244, 246 in bioerodable portion 242 are staggered relative to one another. Staggering a region having a lesser flexibility relative to another region of lesser flexibility may prevent the coil from unwinding while simultaneously allowing the coil (spring) to bend in various directions and to accommodate motion of the airway tissue (e.g. physiological movements, such as eating, breathing, or speaking).

Figure 30:
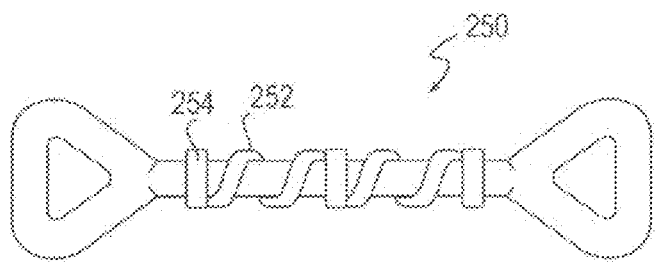
FIG. 30 shows an embodiment of a device with minimal wrapping of the bioerodable portion around the long term implant portion.

The bioerodable material may have one or more than one (a plurality) of coils that wrap around a long axis (e.g. around a long-term elongate implant axis) no times (e.g. be a straight bar or a curve bar), or may wrap around the axis up to 1 time, up to 2 times, up to 3 times, up to 4 times, up to 5 times, up to 10 times, up to 20 times, up to 30 times, up to 40 times, or more than 40 times. FIG. 30 shows an embodiment of implant 250 in which bioerodable material 252 winds around (at least partially envelopes) the long term implant one and a half times. The bioerodable material may partially envelop the long term implant portion (as shown in FIG. 30) or may almost completely or may completely envelop the long term implant portion. The bioerodable material may be coupled with a long term implant at wide region 254 to create a region of lesser flexibility on the bioerodable material.

Figure 31:
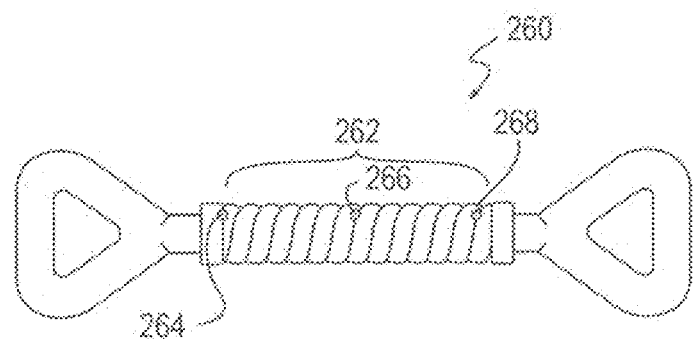
FIG. 31 shows another embodiment of a device with a single spring coupled to itself.

The long term implant portion may have none, one or more than one wide portions that separate narrow portions. The wide portion may have a tensioned configuration and may provide a compressive force to the bioerodable portion such that the bioerodable portion holds the long-term implant portion in a preferred shape. FIG. 31 shows implant 260 with two wide portions and a single spring 262. The single spring (helix) partially envelops a narrow portion and is coupled with itself at two points at bridge 268 near an end of the helix and at bridge 266 near a central portion of the helix. In addition, or instead, the spring may be coupled at the other end of the helix (coil), and/or may be coupled at one or more places along the middle portions of the spring. The bioerodable portion may be coupled with the long term implant though bridge 264 to hold the long-term implant portion in a preferred shape. The bioerodable portion may be coupled with the long-term implant portion is any way.

Figure 32:
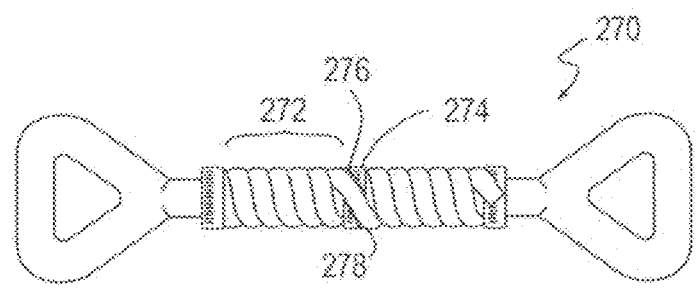
FIG. 32 shows another embodiment of a device according to the invention with the bioerodable portion coupled with the long-term elongate implant portion.

The long-term implant portion may couple with the bioerodable portion in any way (e.g. chemically, mechanically). FIG. 32 shows implant system 270 in which wide portion 274 of the long term, resilient, elongate implant includes channel 276 configured to accept a cross portion 278 of bioerodable material. A channel may grip or hold a cross portion of bioerodable material or the channel may provide a passage for a cross portion without gripping it. A cross portion may be configured along with section 272 of a bioerodable helix to resist a compressive force or provide an expansive force to a long term implant portion, including to channel 276. In one method of manufacturing an implant system with an implant having a resilient (or elongate) implant body including an implant body point and a bioerodable support material configured to hold the resilient (elongate) implant body, the method includes: wrapping the bioerodable support material at least partway around the implant body; and coupling the bioerodable support material with the implant body. The bioerodable support material may be coupled with the implant body using any means (e.g. chemical or mechanical). In one example, the first portion is a narrow portion and the second portion is a channel in a wide portion, the channel configured to hold the bioerodable material, and the bioerodable support material is passed through or along a surface of the channel. The implant body (channel) may hold the bioerodable material or the bioerodable material and the implant body may be fastened together, such as by a lock and key or a chemical coupling.

If different and multiple regions of coils are fused, a range of contraction times of the long term implant portion could be generated. Note that coil diameter also contributes to rate of contraction but may be secondary to coil fusion. In in vitro tests, the durometer of the material influenced contraction in the least significant manner. Nonetheless, taken together these parameters could be used to generate a matrix of physical properties that could influence the timing of the degradation of the coils, as well as match the bending properties of the device as a whole to tongue or other airway implant motion.

Figure 33:
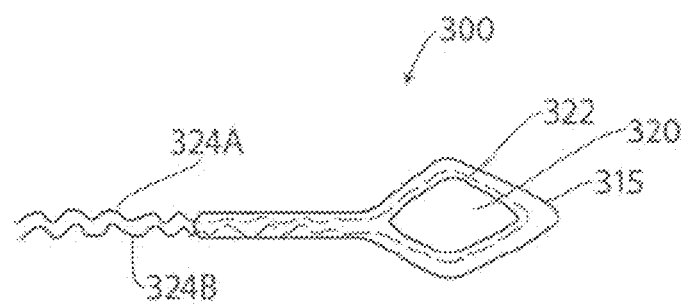
FIG. 33 depicts an end portion of an alternative revisable implant including a cut wire for cutting a tissue plug.
Figure 34:
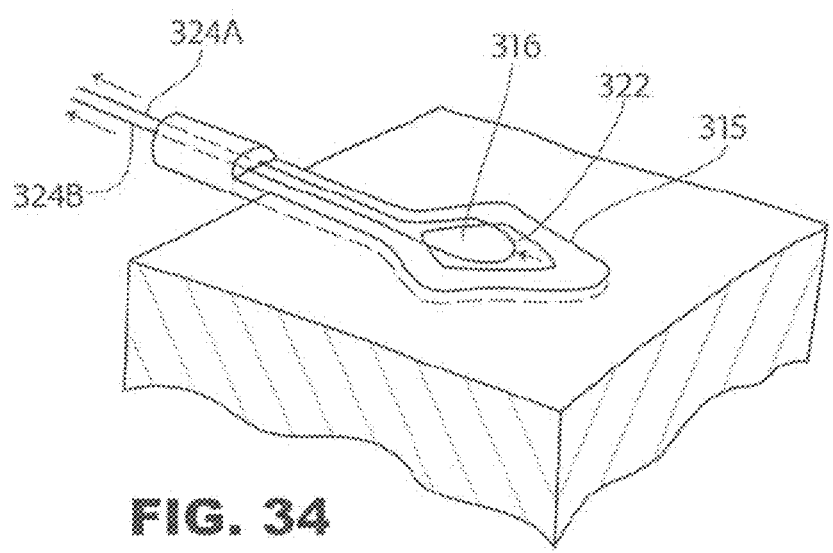
FIG. 34 is a cut-away view depicting the implant of FIG. 14 in a tissue site in the process of actuating the cut wire.

Any of the features described herein may be combined with any other features herein or as is known in the art. For example, any implant or any system may have a region(s) configured to be externally identifiable or visible or made externally identifiable or visible (e.g. by fluoroscopy), such as to a health care provider (physician) to aid in device placement, device tracking, and/or device removal. A region, such as wide sections 108 shown in FIG. 19 A-D for example or at least part of anchor end 104 may be platinum or other identifiable material. An implant or system may have a plurality of regions that are identifiable. In another example, any of the devices may be configured to be easily removable. FIGS. 33 and 34 illustrate another embodiment of revisable OSA implant 300 that includes at least one end with an encircling portion indicated at 315 that encircles or surrounds a tissue plug 316 that grows through an opening 320. In one embodiment, the implant carries a cut wire 322 that extends in a loop with first and second wire ends 324A and 324B extending through one or more passageways in the implant. The cut wire 322 can be embedded in the surface of the implant surrounding the opening 320. As can be seen in FIG. 34, the looped cut wire 322 can be pulled proximally to cut the tissue plug 316 which then will free the implant from its attachment. In FIG. 33, it can be seen that the cut wire ends 324A and 324B can have a serpentine configuration in the medial portion of the implant so as to not interfere with the tensioning and relaxation of the elastomeric medial implant portion during its use. When the cut wire is accessed and pulled relative to the implant 300, the tissue plug 316 can be cut. It should be appreciated that other tools (not shown) may be used to stabilize the implant when actuating the cut wire as in FIG. 34. The cut wire 322 can be any form of fine wire, or abrasive wire or a resistively heated wire coupled to an electrical source (not shown).

Figure 35:
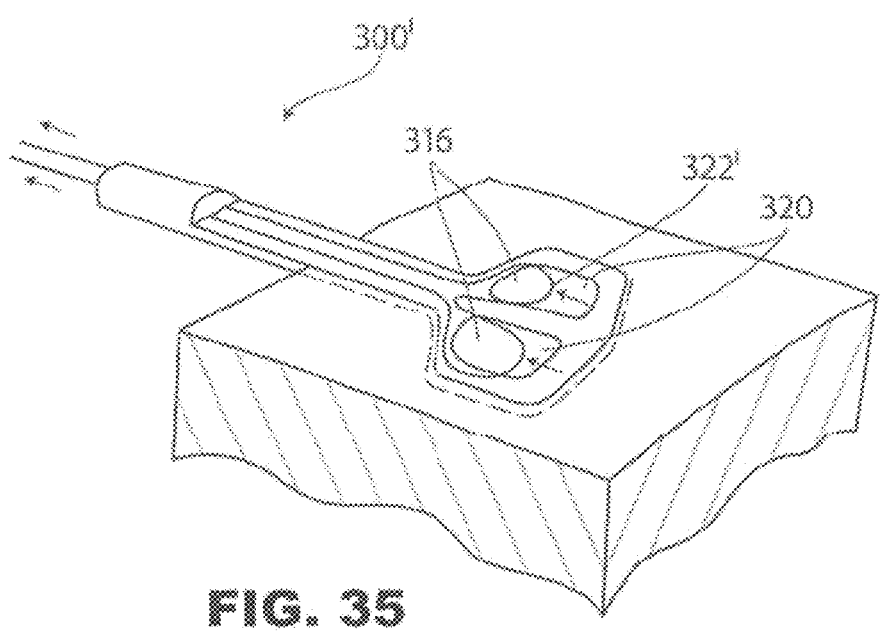
FIG. 35 depicts an end portion of an alternative revisable implant including a cut wire for cutting a plurality of tissue plugs.

FIG. 35 depicts another revisable OSA implant 300' that is similar to that of FIGS. 33-34 with the cut wire 322' configured to cut a plurality of tissue plugs 316 that have grown through openings 320 within an encircling end portion of the implant body.

The devices may alternatively, or additionally, have reinforced anchor portions. The reinforced anchor portions may allow tissue to grow on or through an anchor portion and may serve to better anchor a device in place. The reinforced anchor portions may help hold an implant in place and/or may keep an implant from undergoing undesired stretching.

Figure 36:
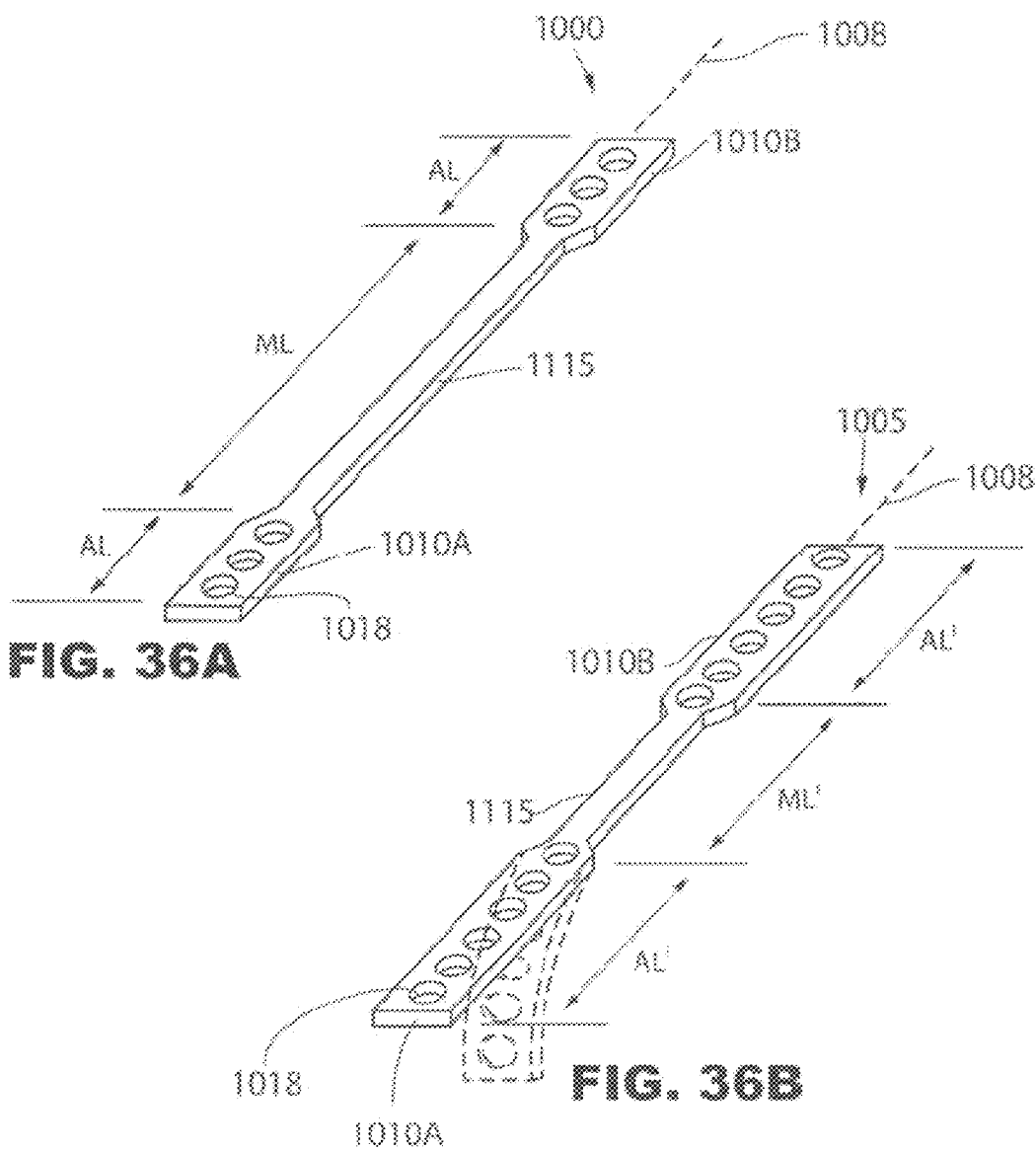
FIGS. 36A-36B depict other embodiments of implant bodies configured with axially inelastic anchoring end portions and an elastic medial portion, wherein the end portions have a substantial axial length relative to the medial portions.

FIGS. 36A and 36B further illustrate that the anchor portion's axial length of AL (or AL') can have a selected relationship to the medial portion's axial length ML (or ML'), and thus the overall implant length which is dependent on the desired amount of axial retraction forces applied by the implant. For example, in FIG. 36A, in one embodiment each anchoring end length AL can be 15% of the overall length of the implant which has a medial portion 1115 configured to apply a retraction force of 3.0 Newtons. FIG. 36B depicts another embodiment wherein each anchoring end length AL' can be 35% of the overall length of the implant and the medial portion 1115 with length ML' can still be configured to apply a retraction force of 3.0 Newtons. In this embodiment, the design in FIG. 36B may be preferred because of the increased anchoring length, which would decrease the likelihood of tissue remodeling over time.

Figure 37:
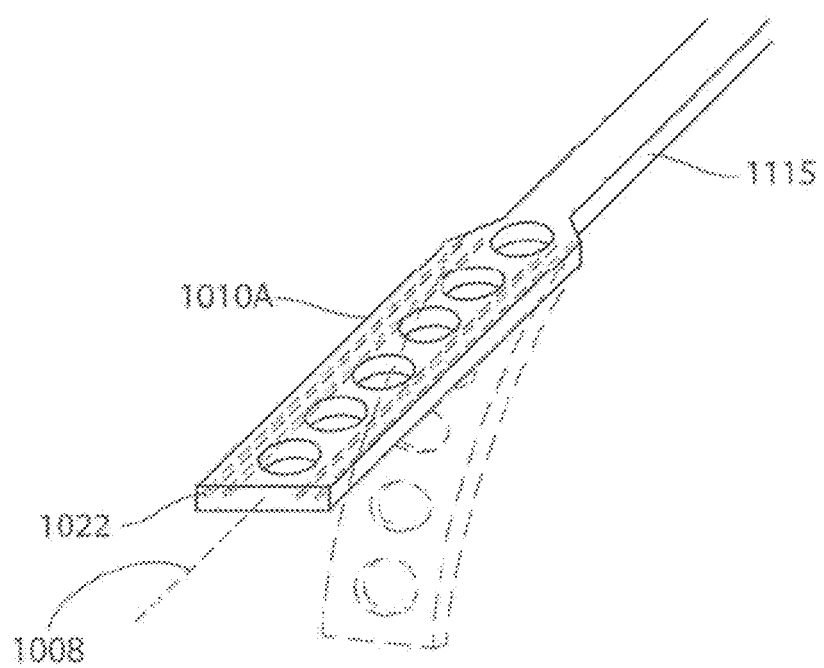
FIG. 37 is an enlarged view of an anchoring end of the implant body of FIG. 36B depicting non-stretchable interior elements.
Figure 38A:
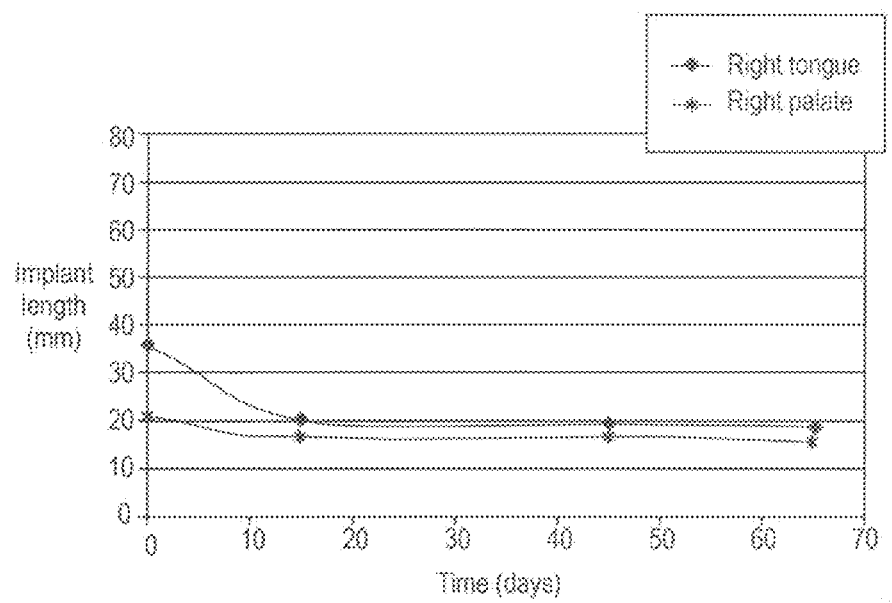
FIGS. 38 A-D show implant length over time after implant placement in the tongue or soft palate.
Figure 38B:
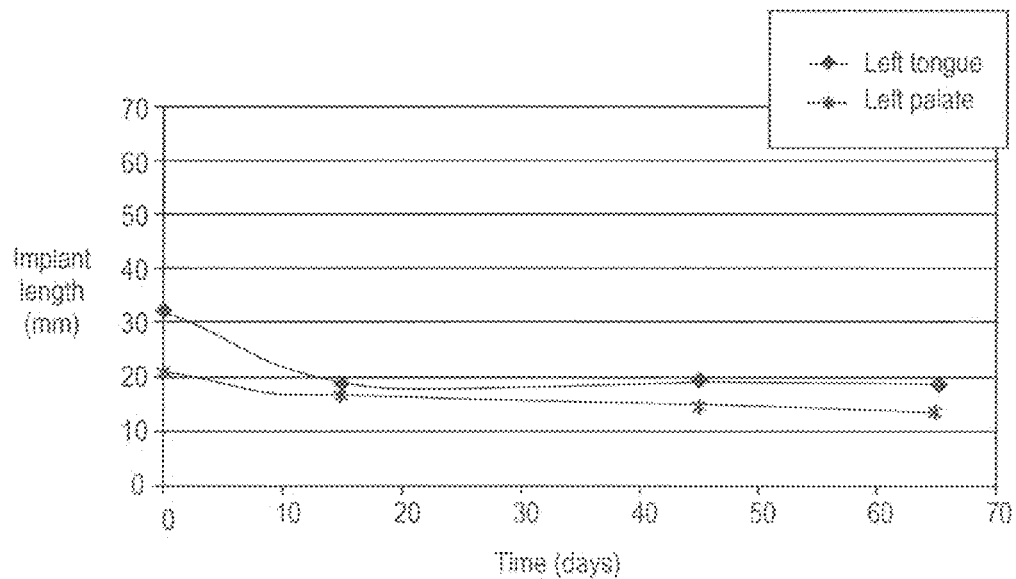
Figure 38C:
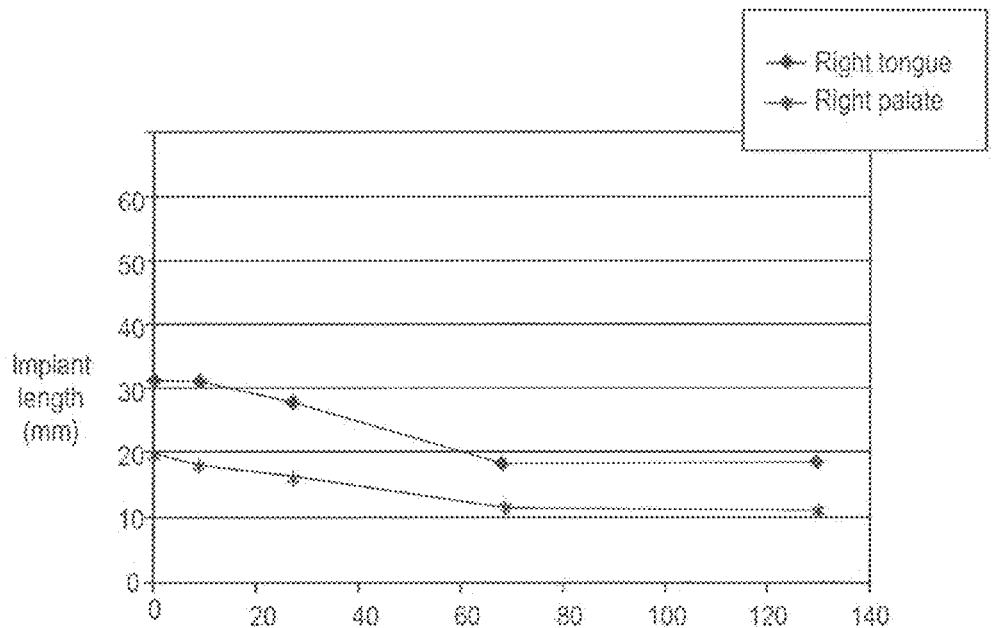
Figure 38D:
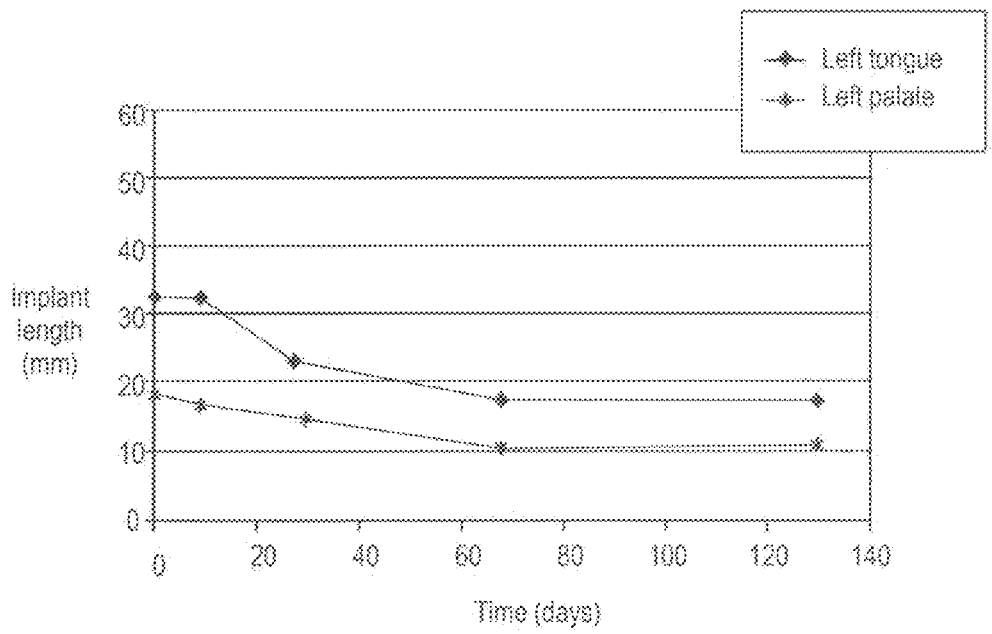

Referring to FIG. 37, it can be seen that an anchoring end portion 1010a of an OSA implant is made axially inelastic by means of non-stretchable reinforcing filaments or elements 1022 embedded therein. Such filaments 1022 can be an inelastic, flexible polymer (e.g., Kevlar®, or polyester), metal wires (e.g. stainless steel, NiTi), carbon fiber or the like. The filaments 1022 can be substantially linear elements or can be knit, woven, non woven, or braided structures as in known in the art. In another embodiment, the anchoring end portion may be made of a non-stretchable material without the addition of reinforcing filaments or elements. As can be understood from FIG. 37, the end portion 1010a is thus axially inelastic but is still flexible and twistable relative to axis 1008.

The devices described herein may be combined with other device features, including, but not limited to those described in U.S. Pat. No. 8,167,787, U.S. 2011/0144421, U.S. 2011/0226262, and U.S. patent application Ser. No. 13/308,449 to Gillis et al. filed Nov. 30, 2011.

Any of the devices or systems described herein may be configured to substantially hold the bioerodable material and/or may be configured to hold the long term implant in an initial (e.g. a first or a non-final) shape or configuration for less than 16 weeks (e.g. between 2 and 6 weeks, between 3 and 5 weeks, or for less than 1 week, less than 2 weeks, less than 3 weeks, less than 4 weeks, less than 5 weeks, less than 6 weeks, less than 7 weeks, or less than 8 weeks) when exposed to a body fluid or a saline solution. A body fluid that the device may be exposed to may be, for example, blood, interstitial fluid, lymph, mucus, nasal exudate or discharge, and/or saliva. A saline solution may be any saline solution, including a buffered saline solution. In one particular example, it is 0.1 M saline (0.1 M sodium chloride). After exposure to a body fluid for a sufficient period of time, an implant may take on a second, final, or therapeutic shape or configuration.

EXAMPLES

Example 1

Implant Contraction Accelerated Testing

An in vitro test system was developed to demonstrate the fatigue behavior of the restricting coils and simulate the expected motion after implantation. While not wishing to be limited to any theory, it is thought that the characteristic motions of the coiled implant when implanted are initially multiplanar bending. While some stretching of the device may occur, contraction is substantially prevented until the supporting coils degrade.

In order to evaluate the relative performance of types of coils, sets of implants with different durometer silicone cores and with coils that were either fused or open-ended within segments were rested. Coils with diameters of 0.009" or 0.013" were tested in 0.1 M saline at 37° C. in a 20 L bath. The coils were made to oscillate by fixing one end and placing the body of the implant in a moving stream such that bending occurred at an approximate frequency of 2 Hz with a randomly oriented 15 degree to 30 degree bending motion. Bacterial growth was inhibited by addition of 0.01% sodium azide. Solutions were replaced each week and refreshed daily to replace fluid lost by evaporation. Temperature was maintained with the use of a submersible thermocouple regulated coil heater.

In general, regardless of the durometer of the silicone core tested, coil segments that were not fused at both ends began to unravel at their distal ends, causing a decrease in the stretched length of the implant from 36+/−1 mm to 21 to 27 mm by day 10 of the test. In contrast, implant systems with coils that were fused relaxed a stretched length of about 36 mm to about 34 mm by day 10.

Silicone cores with unfused coils contracted to 18 mm, which is their relaxed state, by day 15. For the fused coil materials tested, the rate of contraction depended little upon the durometer of the material or the diameter of the coil. The higher durometer (50 D) material tested with 0.013" diameter fused coils contracted the least, contracting to only about 34 mm. 40 D material tested under the same conditions contracted to about 32 mm. This difference is small compared to the contraction levels observed in unfused coils and shows that although use of a higher durometer material can greatly increase the force on the coils, its effect is far less significant than is coil fusion. This suggests that the greatest impact on maintaining stretched implant length and avoiding early (premature) contraction was created by fusing coils.

Example 2

The effect of fusing implant coils together to prevent the coils from prematurely unwinding on the implant contraction rate was further tested using a canine animal model. Comparable implant systems having resilient, long term implants initially held in expanded shapes by coiled bioerodable implant material with (FIGS. 38 C-D) and without (FIGS. 38 A-B) fused coils were placed on both left and right sides of animals' tongues and soft palates and the bioerodable material bioeroded to allow the resilient, long term implants to foreshorten. The implant lengths were measured as a function of length of time since implantation. Noting that the time scales are different, as seen by the more gradually downward sloping curves going from the initial implant lengths (at time=0) to the equilibrium (foreshortened) implant lengths in the results shown with the fused coils placed in the right and left sides of the tongue ("Right tongue" and "Left tongue", respectively) as shown FIGS. 38 C-D compared with the steeper, downwardly sloping lines obtained from the corresponding unfused implants shown in FIGS. 38 A-B, resilient implants with fused bioerodable coils placed in the tongue shortened more slowly and took a longer overall time to reach a (fully) foreshortened length than did resilient without fused bioerodable coils. Systems with fused coils took several weeks (e.g. more than 22 days and possibly as long as 25-40 days or more) to contract to about 20 mm, about the same implant length that systems having unfused coils reached by about 10-14 days after implantation. Comparing results of fused coil implant systems (with unfused coil implant systems in the tongue (FIGS. 38 A-D), bioerodable coil fusion eliminated about 80% of the amount of contraction (foreshortening) observed in the unfused coil system at 14 days. The rate of foreshortening was also slower in implant systems in the soft palate having fused coils compared with implant systems without fused coils (compare results for "Right palate" and "Left palate" in FIGS. 38 A-D).

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An implant system for treating a sleep disorder comprising a bioerodable material and an elongate long term implant, wherein the bioerodable material at least partially envelops the elongate long term implant and resists a compressive force of the long term implant, the bioerodable material comprising a plurality of first regions having a first flexibility and a plurality of second regions having a second, flexibility that is less than the first flexibility.

2. The implant system of claim 1 wherein the bioerodable material comprises a spring having a plurality of coils and the first regions having the first flexibility comprise two coils of the spring.

3. The implant system of claim 2 wherein the second regions having the second, lesser flexibility comprise two points on the coils that are linked with each other.

4. The implant system of claim 1 wherein the second regions of lesser flexibility are configured to maintain the bioerodable material in an enveloping configuration relative to the elongate long term implant.

5. The implant system of claim 1 wherein the regions of lesser flexibility are configured to substantially hold the bioerodable material in an initial shape for a period of time that is less than 16 weeks upon exposure to a body fluid.

6. The implant system of claim 1 wherein the regions of lesser flexibility are configured to substantially hold the bioerodable material in an initial shape for a period of time between 2 and 6 weeks upon exposure to a body fluid.

7. The implant system of claim 1 wherein the regions of lesser flexibility are configured to substantially hold the bioerodable material in an initial shape for a period of time between 3 and 5 weeks upon exposure to a body fluid.

8. An implant system for implanting in airway forming tissue comprising a bioerodable material and an elongate long term implant, wherein the bioerodable material at least partially envelops the elongate long term implant and is linked between a first set of two points on the bioerodable material to form a first bridge, wherein the bioerodable material comprises a spring having a first set of at least two coils and a plurality of points, and the first bridge connects a first set of two points on the spring.

9. The implant system of claim 8 wherein the bioerodable material is linked between a second set of two points on a second set of coils of the spring to form a second bridge.

10. The implant system of claim 9 wherein the second set of coils is at a second end of the spring.

11. The implant system of claim 10 wherein substantially each coil is linked to at least one other coil to form a plurality of bridges.

12. The implant system of claim 9 wherein the first and second bridges are bioerodable.

13. The implant system of claim 8 wherein the two points are on different coils at a first end of the spring.

14. A method of manufacturing a bioerodable implant comprising the steps of:
    wrapping a bioerodable material at least partway around an axis to create a wound bioerodable implant, the bioerodable material comprising two points along the bioerodable material; and
    coupling the two points to each other.

15. The method of claim 14 wherein the axis comprises an elongate long term implant, and the wrapping around an axis comprises wrapping the bioerodable material around the elongate long term implant to create an implant system.

16. The method of claim 15 further comprising applying an expansive force to the elongate long term implant with the bioerodable material to thereby hold the long term implant in an initial shape.

17. The method of claim 14 wherein coupling comprises attaching a bioerodable material to the two points to create a support strut.

18. The method of claim 14 wherein coupling comprises applying at least one of an adhesive, an other chemical, or an energy source to the bioerodable material.

19. An implant system for treating a sleep disorder comprising a bioerodable material and an elongate long term implant, wherein the bioerodable material at least partially envelops the elongate long term implant and resists a compressive force of the long term implant, the bioerodable material comprising a first region having a first flexibility and a second region having a second flexibility, the first flexibility greater than the second flexibility, the greater flexibility caused by discontinuities in the first region.

20. The implant system of claim 19 wherein the bioerodable material comprises a polymer based on lactic acid.

21. The implant system of claim 20 wherein the bioerodable material comprises poly(lactic acid) or poly(DL-lactic-co-glycolic acid).

22. The implant system of claim 19 wherein the elongate long term implant comprises a silicone material.

23. An implant system for treating an airway disorder, comprising:
    a resilient elongate implant body having a first insertion shape and a second therapeutic shape; and
    a bioerodable material comprising two coils that at least partially envelop the resilient elongate implant body, wherein the coils are coupled together to form a coupled coil structure.

24. The implant system of claim 23 wherein the bioerodable material is configured to hold the implant body in the initial insertion shape.

25. The implant system of claim 24 wherein the bioerodable material comprises additional coils continuous with the two coils to thereby form a spring wherein the additional coils of the spring are wrapped around the implant body and the two coils are at an end of the spring.

26. The implant system of claim 25 wherein substantially each coil is coupled to at least one other coil.

27. An implant system for implanting in airway forming tissue comprising a bioerodable material and an elongate long term implant, wherein the bioerodable material at least partially envelops the elongate long term implant and is linked between a first set of two points along the bioerodable material to form a first bridge configured to limit radial expansion of the bioerodable material relative to the implant.

28. The implant system of claim 27 wherein the bioerodable material is configured to hold the elongate long term implant in an initial shape.

29. The implant system of claim 27 wherein the bioerodable material maintains the elongate long term implant in a tensioned initial shape.

30. A method of manufacturing an implant system, the implant having an elongate implant body and a bioerodable support material configured to hold the elongate implant body in a first, elongate shape, the method comprising the steps of:
    wrapping the bioerodable support material at least partway around the implant body; and
    coupling two points along the bioerodable material with each other to create a coupled bioerodable support material.

31. A method of manufacturing a bioerodable implant comprising the steps of:
    wrapping a bioerodable material at least partway around an axis to create a wound bioerodable implant, the bioerodable material comprising two points; and
    coupling the two points to each other, the coupling comprising heating the bioerodable material to thereby melt the two points together.

32. A method of manufacturing a bioerodable implant comprising the steps of:
    wrapping a bioerodable material at least partway around an axis to create a wound bioerodable implant, the bioerodable material comprising two points; and
    coupling the two points, wherein the wound bioerodable implant comprises a helix and the coupling comprises heating the helix to thereby fuse the two points.

* * * * *